US009562259B2

(12) United States Patent
Nitta et al.

(10) Patent No.: US 9,562,259 B2
(45) Date of Patent: Feb. 7, 2017

(54) METHOD OF ANALYZING CHROMOSOMAL INVERSIONS

(75) Inventors: Hiro Nitta, Oro Valley, AZ (US); Mike Farrell, Tucson, AZ (US); Wenjun Zhang, Tucson, AZ (US); Tom Grogan, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/417,522

(22) Filed: Mar. 12, 2012

(65) Prior Publication Data
US 2012/0237930 A1    Sep. 20, 2012

Related U.S. Application Data

(60) Provisional application No. 61/452,347, filed on Mar. 14, 2011.

(51) Int. Cl.
*C12Q 1/68*       (2006.01)
*G01N 33/53*      (2006.01)

(52) U.S. Cl.
CPC ......... *C12Q 1/6841* (2013.01); *C12Q 1/6827* (2013.01)

(58) Field of Classification Search
None
See application file for complete search history.

(56) References Cited

U.S. PATENT DOCUMENTS

| | | |
|---|---|---|
| 4,711,955 A | 12/1987 | Ward et al. |
| 4,772,691 A | 9/1988 | Herman |
| 4,774,339 A | 9/1988 | Haugland et al. |
| 4,888,278 A | 12/1989 | Singer et al. |
| 5,132,432 A | 7/1992 | Haugland et al. |
| 5,187,288 A | 2/1993 | Kang et al. |
| 5,248,782 A | 9/1993 | Haugland et al. |
| 5,258,507 A | 11/1993 | Cruickshank et al. |
| 5,262,357 A | 11/1993 | Alivisatos et al. |
| 5,274,113 A | 12/1993 | Kang et al. |
| 5,328,824 A | 7/1994 | Ward et al. |
| 5,338,854 A | 8/1994 | Kang et al. |
| 5,427,932 A | 6/1995 | Weier et al. |
| 5,433,896 A | 7/1995 | Kang et al. |
| 5,447,841 A | 9/1995 | Gray et al. |
| 5,451,663 A | 9/1995 | Kang et al. |
| 5,472,842 A | 12/1995 | Stokke et al. |
| 5,505,928 A | 4/1996 | Alivisatos et al. |
| 5,571,018 A | 11/1996 | FitzGerald |
| 5,650,327 A | 7/1997 | Copeland et al. |
| 5,654,200 A | 8/1997 | Copeland et al. |
| 5,690,807 A | 11/1997 | Clark, Jr. et al. |
| 5,696,157 A | 12/1997 | Wang et al. |
| 5,759,808 A | 6/1998 | Casterman et al. |
| 5,800,988 A | 9/1998 | Casterman et al. |
| 5,800,996 A | 9/1998 | Lee et al. |
| 5,830,912 A | 11/1998 | Gee et al. |
| 5,840,526 A | 11/1998 | Casterman et al. |
| 5,874,541 A | 2/1999 | Casterman et al. |
| 5,990,479 A | 11/1999 | Weiss et al. |
| 6,005,079 A | 12/1999 | Casterman et al. |
| 6,015,695 A | 1/2000 | Casterman et al. |
| 6,048,616 A | 4/2000 | Gallagher et al. |
| 6,114,038 A | 9/2000 | Castro et al. |
| 6,130,101 A | 10/2000 | Mao et al. |
| 6,207,392 B1 | 3/2001 | Weiss et al. |
| 6,225,198 B1 | 5/2001 | Alivisatos et al. |
| 6,274,323 B1 | 8/2001 | Bruchez et al. |
| 6,280,929 B1 | 8/2001 | Gray et al. |
| 6,296,809 B1 | 10/2001 | Richards et al. |
| 6,306,736 B1 | 10/2001 | Alivisatos et al. |
| 6,352,861 B1 | 3/2002 | Copeland et al. |
| 6,500,622 B2 | 12/2002 | Bruchez et al. |
| 6,602,671 B1 | 8/2003 | Bawendi et al. |
| 6,649,138 B2 | 11/2003 | Adams et al. |
| 6,670,113 B2 | 12/2003 | Hainfeld |
| 6,682,596 B2 | 1/2004 | Zehnder et al. |
| 6,689,338 B2 | 2/2004 | Kotov |
| 6,709,929 B2 | 3/2004 | Zhang et al. |
| 6,716,979 B2 | 4/2004 | Diwu et al. |
| 6,815,064 B2 | 11/2004 | Treadway et al. |
| 6,827,901 B2 | 12/2004 | Copeland et al. |
| 6,855,202 B2 | 2/2005 | Alivisatos et al. |
| 6,914,256 B2 | 7/2005 | Zhang et al. |
| 6,927,069 B2 | 8/2005 | Weiss et al. |
| 6,942,970 B2 | 9/2005 | Isola et al. |
| 6,943,029 B2 | 9/2005 | Copeland et al. |
| 7,306,916 B2 | 12/2007 | Poulsen et al. |
| 7,964,345 B2 * | 6/2011 | Palanisamy .......... C12Q 1/6841 435/6.11 |
| 2003/0165951 A1 | 9/2003 | Bruchez, Jr. et al. |
| 2003/0211630 A1 | 11/2003 | Richards et al. |

(Continued)

FOREIGN PATENT DOCUMENTS

| | | |
|---|---|---|
| WO | 99/26299 | 5/1999 |
| WO | 2005/001889 A2 | 1/2005 |

OTHER PUBLICATIONS

Hattinger et al. Cytogenetics Cell Genet. 2001.93: 29-35.*
Osborne et al. Nature Genetics. Oct. 29, 2001. 29: 321-325.*
Colleoni et al Am J Pathology. 2000. 156: 781-789.*
Frohnauer et al (Molec Cytogenetics. Nov. 5, 2010. 3:21.*
Shinichi Murata et al. Soshiki Daibo Kagaku. 2006. pp. 63-71 and certified English translation.*
Beltz et al, "Isolation of Multigene Families and Determinatin of Homologies by Filter Hybridization Methods," Methods in Enzymology, 1983, vol. 100, p. 266-285.
Blough et al, "Characterization of Multiple 12p Rearrangements in Testicular Germ Cell Tumor Cell Line 833K and Its Subclone 64CP by Chromosome Microdissection," Cancer Genet Cytogenet, 1998, vol. 104, p. 24-29.
Brown et al, "Fluorescent in situ hybridization on tissue microarrays: challenges and solutions," J. Mol. Hist. 2007, vol. 38, p. 151-157.
Bruchez, Jr. et al, "Semiconductor Nanocrystals as Fluorescent Biological Labels," Science, 1998, vol. 281, p. 2013-2016.

(Continued)

*Primary Examiner* — Carla Myers
(74) *Attorney, Agent, or Firm* — Ventana Medical Systems, Inc.

(57) ABSTRACT

The present disclosure relates to systems and methods for analyzing chromosomal translocations, and in particular to analysis of chromosomal translocation by in situ hybridization.

13 Claims, 3 Drawing Sheets

(56) References Cited

U.S. PATENT DOCUMENTS

| | | | |
|---|---|---|---|
| 2004/0052685 | A1 | 3/2004 | Richards et al. |
| 2004/0265922 | A1 | 12/2004 | Bieniarz et al. |
| 2005/0012182 | A1 | 1/2005 | Jang et al. |
| 2005/0100976 | A1 | 5/2005 | Bieniarz et al. |
| 2006/0246523 | A1 | 11/2006 | Bieniarz et al. |
| 2006/0246524 | A1 | 11/2006 | Bauer et al. |
| 2008/0057513 | A1 | 3/2008 | Farrell |
| 2008/0268462 | A1 | 10/2008 | Kosmeder et al. |
| 2008/0305497 | A1 | 12/2008 | Kosmeder et al. |
| 2010/0136652 | A1 | 6/2010 | Bieniarz et al. |
| 2011/0160076 | A1 | 6/2011 | Alexander et al. |

OTHER PUBLICATIONS

Chan et al, "Quantum Dot Bioconjugates for Ultrasensitive Nonisotopic Detection," Science, 1998, vol. 281, p. 2016-2018.

Ferguson et al, "Meiotic Segregation of Chromosomes in Sperm from Carriers of Reciprocal and Robertsonian Translocations," Fertility and Sterility, Sep. 2006, vol. 86, No. Suppl. 2, p. 945.

Heyduk et al, "Thiol-Reactive, Luminescent Europium Chelates: Luminescence Probes for Resonance Energy Transfer Distance Measurements in Biomolecules," Analytical Biochemistry, 1997, vol. 248, p. 216-227.

Heyduk et al, "Architecture of a Complex between the $\sigma^{70}$ Subunit of *Escherichia coli* RNA Polymerase and the Nontemplate Strand Oligonucleotide," The Journal of Biological Chemistry, 1999, vol. 274, No. 6, p. 3315-3322.

Lichter et al, "Rapid detection of human chromosome 21 aberrations by in situ hybridization," Proc. Natl. Acad. Sci., Dec. 1988, vol. 85, p. 9664-9668.

Makretsov et al, "A Fluorescence In Situ Hybridization Study of ETV6-NTRK3 Fusion Gene in Secretory Breast Carcinoma," Genes, Chromosomes & Cancer, 2004, vol. 40, p. 152-157.

Martin-Subero et al, "Chromosomal Breakpoints Affecting Immunoglobulin Loci Are Recurrent in Hodgkin and Reed-Sertnberg Cells of Classical Hodgkin Lymphoma," Cancer Res., 2006, vol. 66, p. 10332-10338.

Nitta et al, "Automated brightfield break-apart in situ hybridization (ba-ISH) application: ALK and MALTI1 genes as models," Methods, 2010, vol. 52, p. 352-358.

Pienkowska-Grela et al, "Partial trisomy 11, dup(11(q23a13), as a defect characterizing lymphomas with Burkitt pathomorpholoy without MYC gene rearrangement," Med. Oncol., 2011, vol. 28, p. 1589-1595.

Pinkel et al, "Cytogenetic analysis using quantitative, high-sensitivity, fluorescence hybridization," Proc. Natl. Acad. Sci, May 1986, vol. 83, p. 2934-2938.

Pinkel et al, "Fluorescence in situ hybridization with human chromosome-specific libraries: Detection of trisomy 21 and translocations of chromosome 4," Proc. Natl. Acad. Sci., Dec. 1988, vol. 85, p. 9138-9142.

Poddighe et al, "Human papilloma virus detection by in situ hybridisation signal amplification based on biotinylated tyramine deposition," J. Clin. Pathol. Mol. Pathol., 1996, vol. 49, p. M340-M344.

Ried et al, "Specific Metaphase and Interphase Detection of the Breakpoint Region in 8q24 of Burkitt Lymphoma Cells by Triple-Color Fluorescence In Situ Hybridzation," Genes, Chromosomes & Cancer, 1992, vol. 4, p. 69-74.

Renné et al, "Molecular Cytogenetic Analyses of Immunoglobulin Loci in Nodular Lymphocyte Predominant Hodgkin's Lymphoma Reveal a Recurrent IGH-BCL6 Juxtaposition," Journal of Molecular Diagnostics, Aug. 2005, vol. 7, No. 3, p. 352-356.

Szymanowska et al, "BCL2 and BCL3 are recurrent translocation partners of the IGH locus," Cancer Genetics and Cytogentics, 2008, col. 186, p. 110-114.

Tanaka et al, "Detection of Translocation 8;21 on Interphase Cells from Acute Myelocytic Leukemia by Fluorescence In Situ Hybridization and Its Clinical Application," Cancer Genetics and Cytogentics, 1999, vol. 113, p. 29-35.

Tanner et al, "Chromogenic in Situ Hybridization *A Practical Alternative for Fluorescence in Situ Hybridization to Detect HER-2/neu Oncogene Amplification in Archival Breast Cancer Samples*," American Journal of Pathology, Nov. 2000, vol. 157, No. 5, p. 1467-1472.

Vaandrager et al, "Interphase FISH Detection of BCL2 Rearrangements in Follicular Lymphoma Using Breakpoint-Flanking Probes," Genes, Chromosomes & Cancer, 2000, vol. 27, p. 85-94.

Yoshimoto et al, "Three-Color FISH Analysis of TMPRSS2/ERG Fusions in Prostate Cancer Indicates That Genomic Microdeletion of Chromosome 21 is Associated with Rearrangement," Neoplasia, Jun. 2006, vol. 8, No. 6, p. 465-469.

Schildhaus et al, "Novel assays for predictive diagnosis of non small cell lung cancer: Triple color FISH increases sensitivity and specificity of EML4-ALK translocation detection in pulmonary adenocarcinomas; FGFR1 amplifications are detectable by FISH in 21% of squamous cell carcinomas of the lung," Proceedings of the AACR-NCI-EORTC International Conference on Molecular Targets and Cancer Therapeutics; Nov. 12-15, 2011; San Francisco, CA, Philadelphia, PA: AACR; Mol Cancer Ther 2011; 10 (11 Suppl): Abstract nr A200.

Shinichi Murata et al., Soshiki Daibo Kagaku, 2006, pp. 63-71.

\* cited by examiner

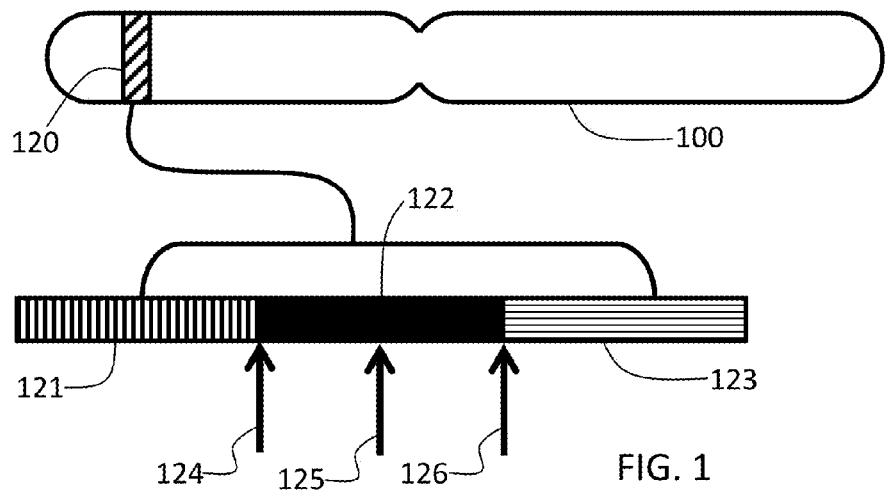
FIG. 1
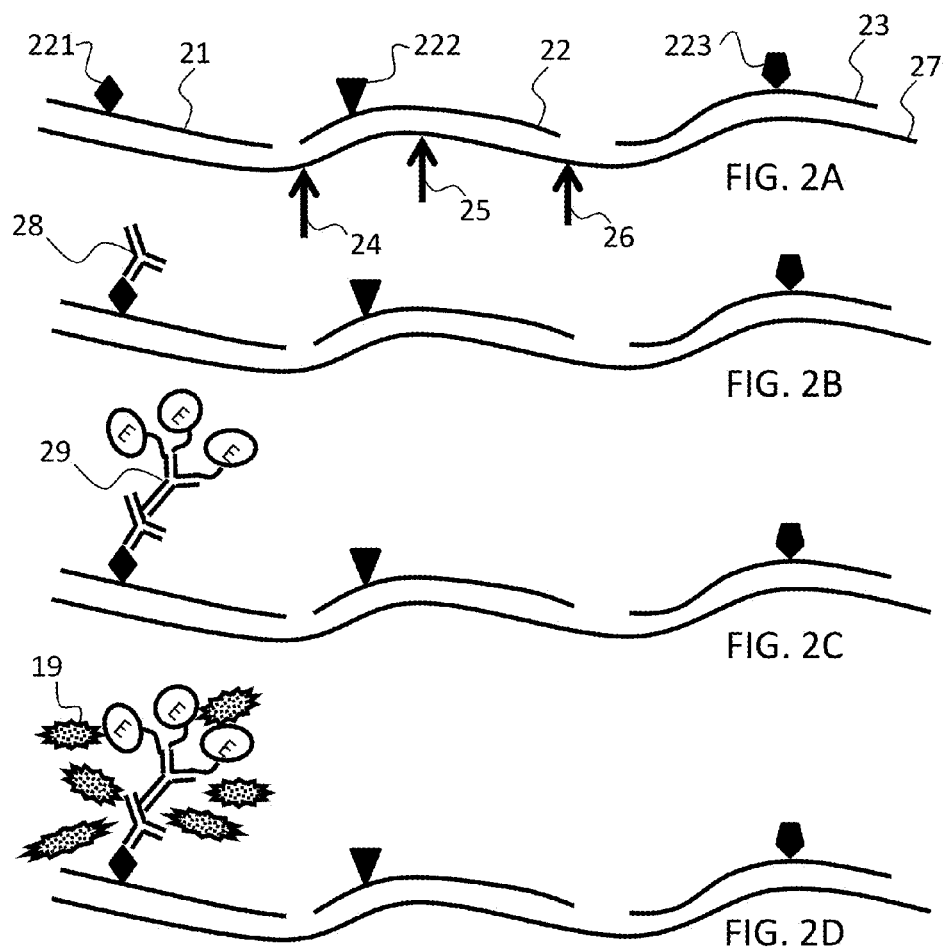
FIG. 2A
FIG. 2B
FIG. 2C
FIG. 2D

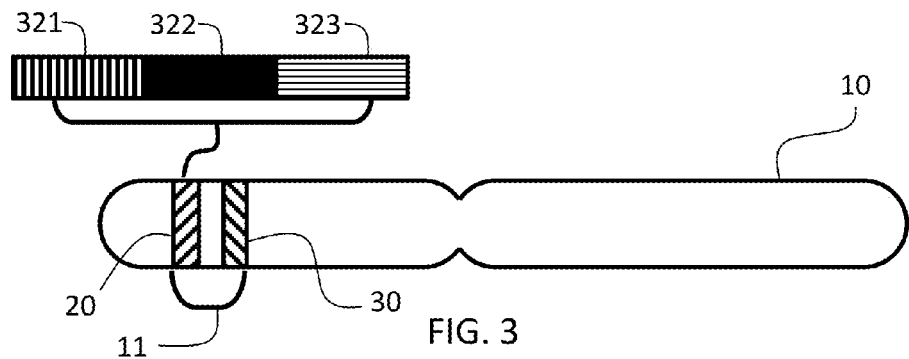
FIG. 3
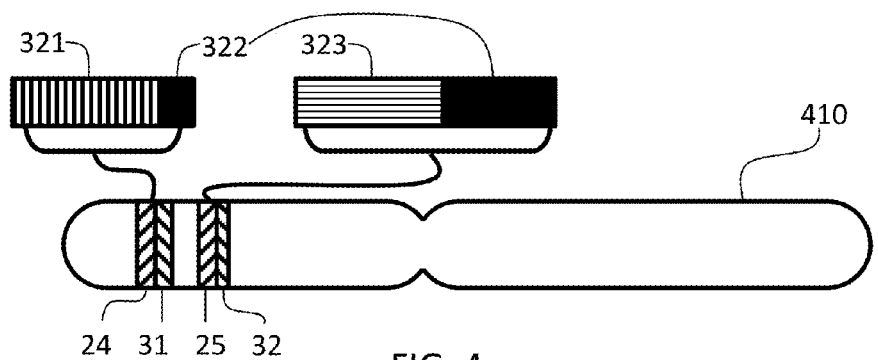
FIG. 4
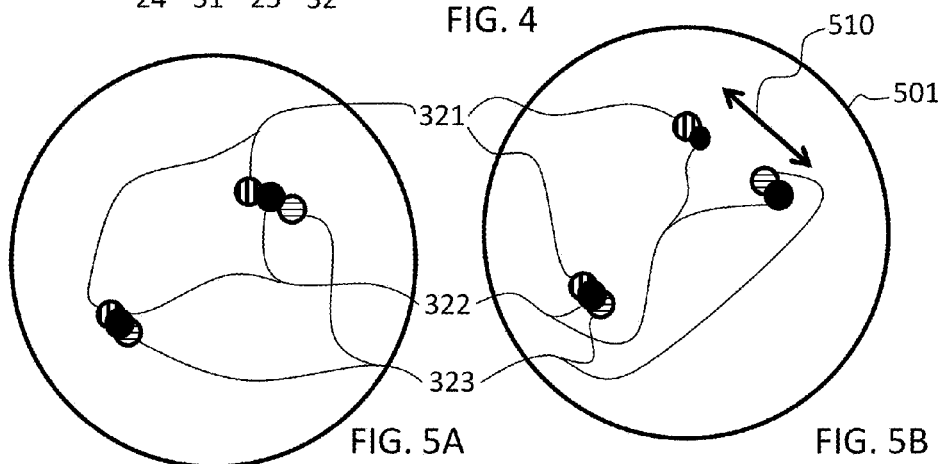
FIG. 5A
FIG. 5B
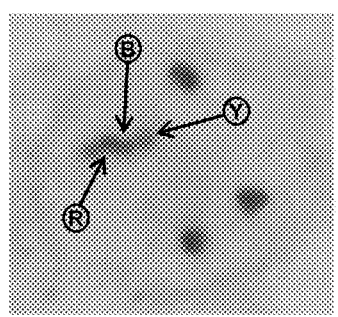
FIG. 6A
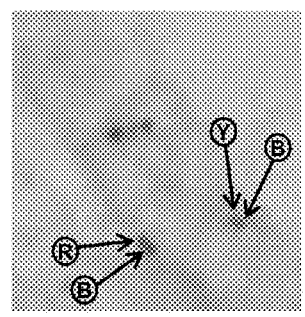
FIG. 6B

METHOD OF ANALYZING CHROMOSOMAL INVERSIONS

CROSS-REFERENCE TO RELATED APPLICATION

This application claims the benefit of the earlier filing date of U.S. Provisional Application No. 61/452,347, which was filed Mar. 14, 2011. The entire disclosure of the provisional application is considered to be part of the disclosure of the following application and is hereby incorporated by reference.

FIELD

The present disclosure relates to systems and methods for analyzing chromosomal translocations, and in particular to analysis of chromosomal translocation by in situ hybridization.

BACKGROUND

The diagnosis, prognosis, and determination of treatment of disease based on the interpretation of tissue or cell samples taken from a diseased organism has expanded dramatically over the past few years. In addition to traditional histological staining techniques and immunohistochemical assays, in situ techniques such as in situ hybridization and in situ polymerase chain reaction are now used to help diagnose disease states in humans. Thus, there are a variety of techniques that can assess not only cell morphology, but also the presence of specific macromolecules within cells and tissues.

Molecular cytogenetic techniques, such as chromogenic in situ hybridization (CISH) combine visual evaluation of chromosomes (karyotypic analysis) with molecular techniques. Molecular cytogenetics methods are based on hybridization of a nucleic acid probe to its complementary nucleic acid within a cell. A probe for a specific chromosomal region will recognize and hybridize to its complementary sequence on a metaphase chromosome or within an interphase nucleus (for example in a tissue sample). Probes have been developed for a variety of diagnostic and research purposes.

Sequence probes hybridize to single copy DNA sequences in a specific chromosomal region or gene. These are the probes used to identify the chromosomal critical region or gene associated with a syndrome or condition of interest. On metaphase chromosomes, such probes hybridize to each chromatid, usually giving two small, discrete signals per chromosome.

Hybridization of sequence probes, such as repeat depleted probes or unique sequence probes (see for example U.S. 2011/0160076, which is hereby incorporated by reference in its entirety for disclosure related to unique sequence probes), has made possible detection of chromosomal abnormalities associated with numerous diseases and syndromes, including constitutive genetic anomalies, such as microdeletion syndromes, chromosome translocations, gene amplification and aneuploidy syndromes, neoplastic diseases as well as pathogen infections. Most commonly these techniques are applied to standard cytogenetic preparations on microscope slides. In addition, these procedures can be used on slides of formalin-fixed paraffin embedded tissue, blood or bone marrow smears, and directly fixed cells or other nuclear isolates.

The information obtained from these assays can be used to diagnose disease in a patient, determine the prognosis of a patient that has a disease, and also to determine the course of treatment for a patient with a disease. In many instances, the presence of a particular marker can be associated with the predicted efficacy of a drug.

Non-small cell lung cancer (NSCLC) is a disease in which malignant (cancer) cells form in the tissues of the lung. NSCLC is actually a group of lung cancers that are named for the kinds of cells found in the cancer and how the cells look under a microscope. The three main types of non-small cell lung cancer are squamous cell carcinoma, large cell carcinoma, and adenocarcinoma. NSCLC is the most common kind of lung cancer.

Squamous cell carcinoma is a cancer that begins in squamous cells, which are thin, flat cells that look like fish scales. This is also called epidermoid carcinoma. Large cell carcinoma is a cancer that may begin in several types of large cells. Adenocarcinoma is a cancer that begins in the cells that line the alveoli and make substances such as mucus. Other less common types of non-small cell lung cancer are: pleomorphic, carcinoid tumor, salivary gland carcinoma, and unclassified carcinoma.

Smoking cigarettes, pipes, or cigars is the most common cause of NSCLC. The earlier in life a person starts smoking, the more often a person smokes, and the more years a person smokes, the greater the risk. If a person has stopped smoking, the risk becomes lower as the years pass.

Tests and procedures to detect, diagnose, and stage non-small cell lung cancer are often done at the same time. The following tests and procedures are generally used: Chest x-ray; CBC; Sputum test to look for cancer cells; Bone scan; CT scan of the chest; MRI of the chest; Positron emission tomography (PET) scan; and Thoracentesis. In some instances, biopsies are taken and analyzed. If the biopsy reveals the presence of lung cancer, more imaging tests will be done to determine the stage of the cancer. Stage relates to the size of the tumor and the extent to which it has spread. Non-small cell lung cancer is divided into five stages: Stage 0—the cancer has not spread beyond the inner lining of the lung; Stage I—the cancer is small and has yet to spread to the lymph nodes; Stage II—the cancer has spread to some lymph nodes near the original tumor; Stage III—the cancer has spread to nearby tissue or spread to far away lymph nodes; Stage IV—the cancer has spread to other organs of the body such as the other lung, brain, or liver.

There are many different types of treatment for non-small cell lung cancer. Treatment depends upon the stage of the cancer. Surgery is the often the first line of treatment for patients with non-small cell lung cancer that has not spread beyond nearby lymph nodes. The surgeon may remove: One of the lobes of the lung (lobectomy); only a small part of the lung (wedge or segment removal); the entire lung (pneumonectomy). Some patients need chemotherapy. Chemotherapy uses drugs to kill cancer cells and stops new ones from growing. Chemotherapy alone is often used when the cancer has spread (stage IV).

In some instances, a genetic analysis is done to determine the best course of treatment for NSCLC. For example, some patients with particular mutations in the EGFR gene respond to EGFR tyrosine kinase inhibitors such as gefitinib. As another example, the 7% of NSCLC with EML4-ALK translocations may benefit from ALK inhibitors which are in clinical trials.

Break-apart probe systems have been used for analysis of tissues from NSCLC patients. However, due to the nature of the chromosomal rearrangements that occur in NSCLC, there can be a problem with false positive results, especially where the rearrangement is within the same chromosome, such as an inversion. In these cases, it may not be possible to properly resolve the signals from each set of break-apart probes. The signals can appear as two separate signals even though no rearrangement has occurred. This can be a real problem, both due to obtaining incorrect results and the scarcity of biopsy material. Three color systems have been used for chromosomal analysis. See, e.g., Makretsov et al., Genes, Chromosomes and Cancer, 40:152-57 (2004); Martin-Subero, et al., Cancer Res., 66(21):10332-38 (2006); Yoshimoto et al., Neoplasia 8(6):465-69 (2006); Renne et al., J. Mol. Diagnost., 7(3): 352-56 (2005). However, none of these systems have been applied to solve problems associated with false positive results in break-apart probe systems. Break-apart probe systems which address the problem of false positive results would provide a benefit to patients afflicted with cancer.

SUMMARY

The present disclosure relates to systems and methods for analyzing chromosomal translocations, and in particular to analyzing chromosomal translocation by in situ hybridization.

In illustrative embodiments, a method for analyzing a sample for a chromosomal translocation associated with a breakpoint comprises contacting the sample with a first nucleic acid probe comprising a first sequence configured to hybridize to genomic DNA located 5' to the breakpoint, a second nucleic acid probe comprising a second sequence configured to hybridize to genomic DNA located 3' to the breakpoint, and a third nucleic acid probe comprising a third sequence configured to hybridize to genomic DNA adjacent to the breakpoint. The method further comprises establishing conditions suitable for the probes to hybridize to the genomic DNA in the sample and detecting hybridization of the probes by detecting a first signal associated with the first nucleic acid probe, a second signal associated with the second nucleic acid probe, and a third signal associated with the third nucleic acid probe. In one embodiment, the method further comprises identifying a sample order and orientation, the sample order and orientation being a sequence of the first signal, the second signal, and the third signal longitudinally arranged along a chromosome. In another embodiment, the method further comprises comparing the sample order and orientation with a control order and orientation. In another embodiment, the control order and orientation is a sequence of the first signal, the second signal, and the third signal longitudinally arranged along a chromosome, wherein the chromosome is known to be devoid of a chromosomal translocation associated with a breakpoint.

In illustrative embodiments, the third sequence is configured to hybridize to genomic DNA 5' and adjacent to the breakpoint, and comparing the sample order and orientation with a control order and orientation includes establishing whether the sample order and orientation includes inversion of the first signal and the third signal as compared to the control order and orientation. In one embodiment, the third sequence is configured to hybridize to genomic DNA 3' and adjacent to the breakpoint, and comparing the sample order and orientation with a control order and orientation includes establishing whether the sample order and orientation includes inversion of the second signal and the third signal as compared to the control order and orientation. In another embodiment, the third sequence is configured to hybridize to genomic DNA adjacent to the breakpoint located both 5' and 3' of the breakpoint, and comparing the sample order and orientation with a control order and orientation includes establishing whether the sample order and orientation includes inversion of the either the first signal or the second signal with the third signal as compared to the control order and orientation.

In illustrative embodiments, the method comprises determining the control order and orientation by analyzing a control known to be devoid of the chromosomal translocation associated with the breakpoint comprising, wherein determining includes contacting the control with the first nucleic acid probe comprising the first sequence configured to hybridize to genomic DNA located 5' to the breakpoint, the second nucleic acid probe comprising the second sequence configured to hybridize to genomic DNA located 3' to the breakpoint, and the third nucleic acid probe comprising the third sequence configured to hybridize to genomic DNA adjacent to the breakpoint. The method further comprises establishing conditions suitable for the probes to hybridize to the genomic DNA in the control and detecting hybridization of the probes by detecting a first signal associated with the first nucleic acid probe, a second signal associated with the second nucleic acid probe, and a third signal associated with the third nucleic acid probe.

In illustrative embodiments, the nucleic acid probes comprise nucleic acid selected from the group consisting of RNA, DNA, PNA, LNA and combinations thereof labeled with a detectable moiety. In one embodiment, the detectable moiety is selected from the group consisting of a hapten, an enzyme, a fluorescent molecule, a luminescent molecule and a radioactive molecule. In another embodiment, the detectable moiety is a hapten, and the first, second and third nucleic acid probes are labeled with different first, second and third haptens, respectively. In some embodiments, haptens are selected from the group consisting of biotin, 2,4-dintropheyl (DNP), fluorescein derivatives, digoxygenin (DIG), 5-nitro-3-pyrozolecarbamide (nitropyrazole, NP), 4,5,-dimethoxy-2-nitrocinnamide (nitrocinnamide, NCA), 2-(3,4-dimethoxyphenyl)-quinoline-4-carbamide (phenylquinolone, DPQ), 2,1,3-benzoxadiazole-5-carbamide (benzofurazan, BF), 3-hydroxy-2-quinoxalinecarbamide (hydroxyquinoxaline, HQ), 4-(dimethylamino)azobenzene-4'-sulfonamide (DABSYL), rotenone isoxazoline (Rot), (E)-2-(2-oxo-2,3-dihydro-1H-benzo[b][1,4]diazepin-4-yl) phenozy)acetamide (benzodiazepine, BD), 7-(diethylamino)-2-oxo-2H-chromene-3-carboxylic acid (coumarin 343, CDO), 2-acetamido-4-methyl-5-thiazolesulfonamide (thiazolesulfonamide, TS), and p-methoxyphenylpyrazopodophyllamide (Podo).

In other illustrative embodiments, the method includes detecting that includes contacting the sample antibodies specific to the label haptens, for example, with first, second and/or third antibodies specific for the first, second, and third haptens, respectively. In one embodiment, detecting further comprises detecting haptens (e.g. first, second, and third haptens) using anti-hapten recognition and enzymatic signal amplification.

In illustrative embodiments, a kit for analyzing a sample for a chromosomal translocation associated with a breakpoint comprises a first nucleic acid probe having a sequence configured to hybridize to a portion of the genomic DNA that is located 5' to the breakpoint, a second nucleic acid probe having a sequence configured to hybridize to a portion of the genomic DNA that is located 3' to the breakpoint, and a third nucleic acid probe having a sequence configured to hybridize to a portion of DNA that is adjacent to the breakpoint. In one embodiment, the third nucleic acid probe has a sequence configured to hybridize to a portion of DNA adjacent to and spanning the breakpoint on both the 5' and 3' sides of the breakpoint. In another embodiment, the first, second, and third nucleic acid probes are haptenated with a first, second, and third hapten, the kit further comprising detection reagents configured to enable visualization of the first, second, and third hapten. In another embodiment, the detection reagents are chromogenic detection reagents configured to enable bright-field visualization of the first, second, and third hapten.

In illustrative embodiments, a method for diagnosing a disease associated with a chromosomal translocation associated with a breakpoint in a patient sample comprises contacting the patient sample with a series of nucleic acid probes, the series selected so that in the absence of the chromosomal translocation associated with the breakpoint, the series hybridizes to the patient sample according to a first order and orientation, and so that in the presence of the chromosomal translocation associated with the breakpoint, the series hybridizes to the patient sample according a different order and orientation and detecting whether the series of nucleic acid probes hybridizes to the patient sample according to the first order and orientation, wherein detecting the first order and orientation provides a diagnosis that the patient sample does not have the chromosomal translocation associated with the breakpoint in the patient sample. In one embodiment, the first order and orientation is a predetermined sequence of three signals longitudinally arranged along a chromosome. In another embodiment, detecting includes using chromogenic detection reagents visualized using bright-field imaging.

BRIEF DESCRIPTION OF THE DRAWINGS

FIG. 1 is a schematic depiction of a chromosome showing a breakpoint region and probes configured to hybridize thereto;

FIG. 2(A-D) show a schematic depiction of an exemplary detection scheme;

FIG. 3 is a schematic depiction of a chromosome showing two breakpoint locations at which an inversion chromosomal translocation can occur and probes configured to hybridize thereto;

FIG. 4 is a schematic depiction showing the chromosome of FIG. 3 subsequent to the inversion chromosomal translocation and the resulting localization of the probes;

FIG. 5(A-B) is a magnified top plan view showing the signal reported for (A) wild-type ALK and (B) rearranged ALK as would be seen using triple colorimetric detection and bright-field imaging;

FIG. 6(A-B) are photographic images corresponding to FIG. 5(A-B) respectively;

DEFINITIONS

Figure 7:
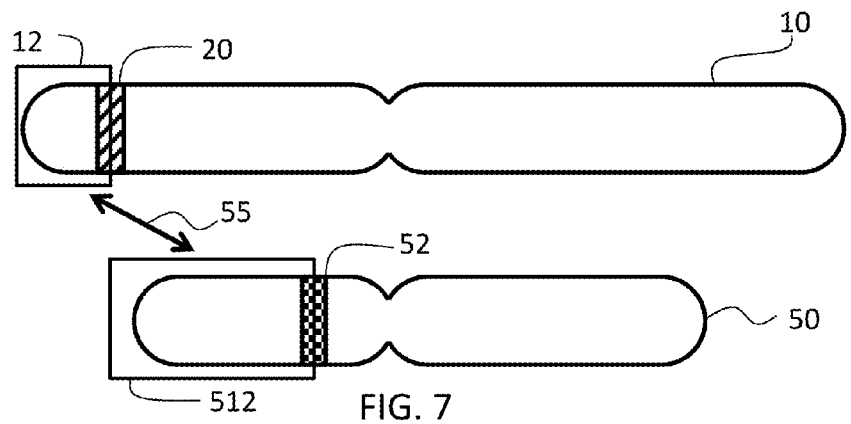
FIG. 7 is a schematic depiction of two chromosomes showing two breakpoint locations at which a rearrangement chromosomal translocation can occur.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a", "an", and "the" include plural referents unless context clearly indicates otherwise. Similarly, the word "or" is intended to include "and" unless the context clearly indicates otherwise. The term "plurality" is used synonymously with the phrase "more than one," that is, two or more. It is further to be understood that all base sizes or amino acid sizes, and all molecular weight or molecular mass values, given for nucleic acids or polypeptides are approximate, and are provided for description. The term "comprises" means "includes." The abbreviation, "e.g.," is derived from the Latin exempli gratia, and is used herein to indicate a non-limiting example. Thus, the abbreviation "e.g.," is synonymous with the term "for example." Although methods and materials similar or equivalent to those described herein can be used in the practice or testing of this disclosure, suitable methods and materials are described below.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ M$^{-1}$ greater, at least $10^4$ M$^{-1}$ greater or at least $10^5$ M$^{-1}$ greater than a binding constant for other molecules in a biological sample.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art. Antibody fragments include proteolytic antibody fragments [such as F(ab')$_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, F(ab)'$_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079-5,874,541; 5,840,526; 5,800,988; and 5,759,808). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3.sup.rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

"Binding or stable binding" refers to the association between two substances or molecules, such as the hybridization of one nucleic acid molecule (e.g., a binding region) to another (or itself) (e.g., a target nucleic acid molecule). A nucleic acid molecule binds or stably binds to a target nucleic acid molecule if a sufficient amount of the nucleic acid molecule forms base pairs or is hybridized to its target nucleic acid molecule to permit detection of that binding.

A nucleic acid molecule is the to be "complementary" with another nucleic acid molecule if the two molecules share a sufficient number of complementary nucleotides to form a stable duplex or triplex when the strands bind (hybridize) to each other, for example by forming Watson-Crick, Hoogsteen or reverse Hoogsteen base pairs. Stable binding occurs when a nucleic acid molecule remains detectably bound to a target nucleic acid sequence (e.g., genomic target nucleic acid sequence) under the required conditions.

Complementarity is the degree to which bases in one nucleic acid molecule (e.g., target nucleic acid probe) base pair with the bases in a second nucleic acid molecule (e.g., genomic target nucleic acid sequence). Complementarity is conveniently described by percentage, that is, the proportion of nucleotides that form base pairs between two molecules or within a specific region or domain of two molecules.

In the present disclosure, "sufficient complementarity" means that a sufficient number of base pairs exist between one nucleic acid molecule or region thereof and a target nucleic acid sequence (e.g., genomic target nucleic acid sequence) to achieve detectable binding. A thorough treatment of the qualitative and quantitative considerations involved in establishing binding conditions is provided by Beltz et al. Methods Enzymol. 100:266-285, 1983, and by Sambrook et al. (ed.), Molecular Cloning. A Laboratory Manual, 2nd ed., vol. 1-3, Cold Spring Harbor Laboratory Press, Cold Spring Harbor, N.Y., 1989.

A "computer implemented algorithm" is an algorithm or program (set of executable code in a computer readable medium) that is performed or executed by a computing device at the command of a user. In the context of the present disclosure, computer implemented algorithms can be used to facilitate (e.g., automate) selection of polynucleotide sequences with particular characteristics, such as identification of repetitive (or other undesired, e.g., background producing) nucleic acid sequences or unique binding regions of a target nucleic acid sequence. Typically, a user initiates execution of the algorithm by inputting a command, and setting one or more selection criteria, into a computer, which is capable of accessing a sequence database. The sequence database can be encompassed within the storage medium of the computer or can be stored remotely and accessed via a connection between the computer and a storage medium at a nearby or remote location via an intranet or the internet. Following initiation of the algorithm, the algorithm or program is executed by the computer, e.g., to select one or more polynucleotide sequences that satisfy the selection criteria. Most commonly, the selected polynucleotide sequences are then displayed (e.g., on a screen) or outputted (e.g., in printed format or onto a computer readable medium).

The terms "conjugating, joining, bonding or linking" refer to covalently linking one molecule to another molecule to make a larger molecule. For example, making two polypeptides into one contiguous polypeptide molecule, or to covalently attaching a hapten or other molecule to a polypeptide, such as an scFv antibody. In the specific context, the terms include reference to joining a specific binding molecule such as an antibody to a signal generating moiety, such as a semi-conductor nanocrystal. The linkage can be either by chemical or recombinant means. "Chemical means" refers to a reaction between the antibody moiety and the effector molecule such that there is a covalent bond formed between the two molecules to form one molecule.

The term "coupled", when applied to a first atom or molecule being "coupled" to a second atom or molecule can be both directly coupled and indirectly coupled. A secondary antibody provides an example of indirect coupling. One specific example of indirect coupling is a rabbit anti-hapten primary antibody that is bound by a mouse anti-rabbit IgG antibody, that is in turn bound by a goat anti-mouse IgG antibody that is covalently linked to a detectable label.

The term "corresponding" in reference to a first and second nucleic acid (for example, a binding region and a target nucleic acid sequence) indicates that the first and second nucleic acid share substantial sequence identity or complementarity over at least a portion of the total sequence of the first and/or second nucleic acid. Thus, a binding region corresponds to a target nucleic acid sequence if the binding region possesses substantial sequence identity or complementarity (e.g., reverse complementarity) with (e.g., if it is at least 80%, at least 85%, at least 90%, at least 95%, or even 100% identical or complementary to) at least a portion of the target nucleic acid sequence. For example, a binding region can correspond to a target nucleic acid sequence if the binding region possesses substantial sequence identity to one strand of a double-stranded target nucleic acid sequence (e.g., genomic target DNA sequence) or if the binding region is substantially complementary to a single-stranded target nucleic acid sequence (e.g. RNA or an RNA viral genome).

A "genome" is the total genetic constituents of an organism. In the case of eukaryotic organisms, the genome is contained in a haploid set of chromosomes of a cell. In the case of prokaryotic organisms, the genome is contained in a single chromosome, and in some cases one or more extra-chromosomal genetic elements, such as episomes (e.g., plasmids). A viral genome can take the form of one or more single or double stranded DNA or RNA molecules depending on the particular virus.

The term "hapten" refers to a molecule, typically a small molecule that can combine specifically with an antibody, but typically is substantially incapable of being immunogenic except in combination with a carrier molecule.

The term "isolated" in reference to a biological component (such as a nucleic acid molecule, protein, or cell), refers to a biological component that has been substantially separated or purified away from other biological components in the cell of the organism, or the organism itself, in which the component naturally occurs, such as other chromosomal and extra-chromosomal DNA and RNA, proteins, cells, and organelles. Nucleic acid molecules that have been "isolated" include nucleic acid molecules purified by standard purification methods. The term also encompasses nucleic acids prepared by amplification or cloning as well as chemically synthesized nucleic acids.

A "label" is a detectable compound or composition that is conjugated directly or indirectly to another molecule to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russell, in Molecular Cloning: A Laboratory Manual, 3rd Ed., Cold Spring Harbor Laboratory Press (2001) and Ausubel et al., in Current Protocols in Molecular Biology, Greene Publishing Associates and Wiley-Intersciences (1987, and including updates).

The term "multiplex" refers to embodiments that allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

A "nucleic acid" is a deoxyribonucleotide or ribonucleotide polymer in either single or double stranded form, and unless otherwise limited, encompasses analogues of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A nucleotide is one monomer in a polynucleotide. A nucleotide sequence refers to the sequence of bases in a polynucleotide.

A nucleic acid "segment" is a subportion or subsequence of a target nucleic acid molecule. A nucleic acid segment can be derived hypothetically or actually from a target nucleic acid molecule in a variety of ways. For example, a segment of a target nucleic acid molecule (such as a genomic target nucleic acid molecule) can be obtained by digestion with one or more restriction enzymes to produce a nucleic acid segment that is a restriction fragment. Nucleic acid segments can also be produced from a target nucleic acid molecule by amplification, by hybridization (for example, subtractive hybridization), by artificial synthesis, or by any other procedure that produces one or more nucleic acids that correspond in sequence to a target nucleic acid molecule. A particular example of a nucleic acid segment is a binding region.

A "probe" or a "nucleic acid probe" is a nucleic acid molecule or set of nucleic acid molecules that is capable of hybridizing with a target nucleic acid molecule (e.g., genomic target nucleic acid molecule) and, when hybridized to the target, is capable of being detected either directly or indirectly. Thus probes permit the detection, and in some examples quantification, of a target nucleic acid molecule. In particular examples, a probe includes a plurality of nucleic acid molecules, which include binding regions derived from the target nucleic acid molecule and are thus capable of specifically hybridizing to at least a portion of the target nucleic acid molecule. A probe can be referred to as a "labeled nucleic acid probe," indicating that the probe is coupled directly or indirectly to a detectable moiety or "label," which renders the probe detectable.

The term "semi-conductor nanocrystal" refers to a nanoscale particle that exhibits size-dependent electronic and optical properties due to quantum confinement. Semi-conductor nanocrystal s have, for example, been constructed of semi-conductor materials (e.g., cadmium selenide and lead sulfide) and from crystallites (grown via molecular beam epitaxy), etc. A variety of semi-conductor nanocrystals having various surface chemistries and fluorescence characteristics are commercially available from Life Technologies (see, for example, U.S. Pat. Nos. 6,815,064, 6,682,596 and 6,649,138). Semi-conductor nanocrystals are also commercially available from eBiosciences and Evident Technologies. Other semi-conductor nanocrystals include alloy semi-conductor nanocrystals such as ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN semi-conductor nanocrystals (Alloy semi-conductor nanocrystals and methods for making the same are disclosed, for example, in US Application Publication No. 2005/0012182 and PCT Publication WO 2005/001889).

A "sample" is a biological specimen containing genomic DNA, RNA (including mRNA), protein, or combinations thereof, obtained from a subject. Examples include, but are not limited to, chromosomal preparations, peripheral blood, urine, saliva, tissue biopsy, surgical specimen, bone marrow, amniocentesis samples and autopsy material. In one example, a sample includes genomic DNA or RNA. In some examples, the sample is a cytogenetic preparation, for example which can be placed on microscope slides. In particular examples, samples are used directly, or can be manipulated prior to use, for example, by fixing (e.g., using formalin).

The term "signal generating moiety" refers to a composition or molecule that generates a signal that is detectable by an assay.

The term "specific binding moiety" refers to a member of a binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4 M^{-1}$ greater or $10^5$ $M^{-1}$ greater than a binding constant for either of the two members of the binding pair with other molecules in a biological sample). Particular examples of specific binding moieties include specific binding proteins (for example, antibodies, lectins, avidins such as streptavidins, and protein A), nucleic acids sequences, and protein-nucleic acids. Specific binding moieties can also include the molecules (or portions thereof) that are specifically bound by such specific binding proteins.

The term "specific binding agent" refers to a molecule that comprises a specific binding moiety conjugated to a signal generating moiety.

A "subject" includes any multi-cellular vertebrate organism, such as human and non-human mammals (e.g., veterinary subjects).

A "target nucleic acid sequence or molecule" is a defined region or particular sequence of a nucleic acid molecule, for example a genome (such as a gene or a region of mammalian genomic DNA containing a gene of interest) or an RNA sequence. In an example where the target nucleic acid sequence is a target genomic sequence, such a target can be defined by its position on a chromosome (e.g., in a normal cell), for example, according to cytogenetic nomenclature by reference to a particular location on a chromosome; by reference to its location on a genetic map; by reference to a hypothetical or assembled contig; by its specific sequence or function; by its gene or protein name, or by any other means that uniquely identifies it from among other genetic sequences of a genome. In some examples, the target nucleic acid sequence is mammalian or viral genomic sequence. In other examples, the target nucleic acid sequence is an RNA sequence.

In some examples, alterations of a target nucleic acid sequence (e.g., genomic nucleic acid sequence) are "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by polynucleotide polymorphisms, and/or the two different forms can be quantitatively distinguishable, such as by the number of copies of the target nucleic acid sequence that are present in a cell.

A "vector" is any nucleic acid that acts as a carrier for other ("foreign") nucleic acid sequences that are not native to the vector. When introduced into an appropriate host cell a vector may replicate itself (and, thereby, the foreign nucleic acid sequence) or express at least a portion of the foreign nucleic acid sequence. In one context, a vector is a linear or circular nucleic acid into which a target nucleic acid sequence of interest is introduced (for example, cloned) for the purpose of replication (e.g., production) and/or manipulation using standard recombinant nucleic acid techniques (e.g., restriction digestion). A vector can include nucleic acid sequences that permit it to replicate in a host cell, such as an origin of replication. A vector can also include one or more selectable marker genes and other genetic elements known in the art. Common vectors include, for example, plasmids, cosmids, phage, phagemids, artificial chromosomes (e.g., BAC, PAC, HAC, YAC) and hybrids that incorporate features of more than one of these types of vectors. Typically, a vector includes one or more unique restriction sites (and in some cases a multi-cloning site) to facilitate insertion of a target nucleic acid sequence.

DETAILED DESCRIPTION

The present disclosure relates to systems and methods for analyzing chromosomal rearrangements, and in particular to analysis of chromosomal rearrangements by in situ hybridization. Chromosomal rearrangements place genes in new linkage relationships and generate chromosomes without normal pairing partners. The present disclosure is not limited to the analysis of any particular type of chromosomal rearrangement. In some embodiments, the chromosomal rearrangement occurs within the same chromosome. An example of this type of rearrangement is an inversion. In some embodiments, the rearrangement is a translocation. In a translocation, a segment from one chromosome is transferred to a nonhomologous chromosome or to a new site on the same chromosome. Nonreciprocal translocations are one-way translocations in which a chromosomal segment is transferred to a nonhomologous chromosome. Reciprocal translocations, on the other hand, involve the exchange of segments from two nonhomologous chromosomes. A gene fusion may be created when the rearrangement joins two otherwise separated genes, the occurrence of which is common in cancer. The chromosomal breakpoint is the region of the chromosome where the double strand of the normally arranged chromosome is broken so that the rearrangement can occur. Translocation requires two double strand breaks.

The present disclosure provides probes and probe systems for use in detection of a target gene sequence in a biological sample. In preferred embodiments, the target sequence is a gene and surrounding sequences (5' and 3') that are prone to rearrangement. Depending on the chromosomal breakpoints, a rearrangement can result in the disruption or misregulation of normal gene function. These molecular rearrangements, in many cases, are considered to be the primary cause of various cancers. Indeed, over the past few decades, clinical cytogeneticists have been able to link specific chromosome breakpoints to clinically defined cancers, including subtypes of leukemias, lymphomas, and sarcomas. Virtually all of the rearrangements observed in tumors have arisen through somatic mutations, so these are not inherited in families.

Analyses of the DNA sequences surrounding many of these rearrangement breakpoints have provided important mechanistic insights into cancer. In some instances, the rearrangement places the coding sequence of a first gene in proximity to the regulatory sequence for a second gene. The first rearrangement of this kind to be described was a rearrangement involving chromosomes 8 and 14 in patients with Burkitt's lymphoma. This particular rearrangement places the MYC proto-oncogene from chromosome 8 under the control of the powerful immunoglobin heavy chain gene (IGH) promoter on chromosome 14. The MYC protein normally triggers signals for cell proliferation, and the rearrangement causes high levels of MYC overexpression in lymphoid cells, where the IGH promoter is normally active.

In other cancers, rearrangements fuse the coding sequences of two genes together to generate potent oncogenes. An example of historic interest is the Philadelphia chromosome, which was initially identified as a minute, or unusually small, chromosome in patients with chronic myelogenous leukemia (CML). The Philadelphia chromosome is actually a product of a reciprocal translocation involving small segments at the ends of the q arms of chromosomes 9 and 22. Subsequent molecular analyses involving multiple laboratories revealed that the translocation fused the coding sequence of the BCR (breakpoint cluster region) gene on chromosome 22 with the coding sequence of the ABL gene on chromosome 9. The BCR-ABL fusion protein encoded by the chimeric gene is a protein tyrosine kinase that constitutively activates signaling pathways involved in cell growth and proliferation. Knowledge of this particular breakpoint has led to a successful treatment for CML, because investigators were able to use the sequence information to overexpress and crystallize the BCR-ABL protein, which in turn led to the development of drugs that inhibit this protein's activity.

In some preferred embodiments, the probes and probe systems are utilized for in situ hybridization procedures, for example, fluorescence in situ hybridization (FISH), colorimetric in situ hybridization (CISH), and silver in situ hybridization (SISH). In some embodiments, the biological sample includes a tissue section (such as obtained by biopsy) or a cytology sample (such as a Pap smear or blood smear). Other types of assays in which the disclosed probes and probe systems can be used are readily apparent to those skilled in the art, and particular examples are discussed below.

In some preferred embodiments, the probe systems comprise at least three probes for analysis of a particular target sequence that comprises a chromosomal breakpoint. In preferred embodiments, each probe preferably comprises a plurality of probes that hybridize to a defined area of the genomic DNA. In preferred embodiments, the probe sets are designed with a bioinformatic tool such as the Human Genome Browser and Repeat Masker. In preferred embodiments, repetitive elements are eliminated from the probe design. In some preferred embodiments, the probes are synthesized by polymerase chain reaction (PCR) processes. For example, in some embodiments, the Primer3 program (on the world wide web at primer3.sourceforge.net) is used to design primers to the unique sequences across the defined area of the chromosome. In some embodiments, the designed PCR fragments and primers are analyzed for similarity to the human genome and transcripts, for example, with Human BLAT and Blastnt programs (on the world wide web at genome.ucsc.edu/cgi-bin/hgBlat). Fragments that exhibit high similarity to other regions (i.e., other defined areas of the chromosome to which other probes are being designed) are excluded and all PCR fragments are verified by sequencing. In some preferred embodiments, the PCR fragments are ligated, random amplified, and labeled by nick translation using a nucleotide (e.g., dUTP or dCTP) conjugated to a hapten (described in more detail below).

Referring now to FIG. 1, shown is a schematic representation of a chromosome 100 having a breakpoint region 120. Across breakpoint region 120, a first nucleic acid probe 121, a second nucleic acid probe 123, and a third nucleic acid probe 122 may be configured to hybridize to breakpoint region 120. Arrows (124, 125, 126) are illustrative breakpoint locations for a breakpoint in three exemplary probe configurations. In one embodiment, probes (121, 122, 123) are configured to place the breakpoint at the 5' end of probe 121 and at the 3' end of probe 122 as is shown by arrow 124. Similarly, a probe configuration placing the breakpoint at the 3' end of probe 123 and at the 5' end of probe 122 is shown by arrow 126. In another embodiment, a probe configuration placing the breakpoint within the span of probe 122 is shown by arrow 125. The probes can be configured to place the breakpoint in several different locations in the context of the probes. Breakpoint locations shown by the arrows (124, 125, 126) are merely exemplary of locations understood at this time to be useful. Localization of the breakpoint within probe 121 or probe 123 is also reasonable, although it may not be a preferred embodiment. In illustrative embodiments, the probes are configured to give rise to distinct signals. Accordingly, FIG. 1 shows the probes with distinct shading (e.g. probe 121 depicted with vertical striping, probe 122 is depicted as solid black, and probe 123 is depicted with horizontal striping). In some embodiments, these probes will be configured to include labels so that they are visually distinguished from each other. While not being limited to a particular detection approach, FIG. 2(A-D) show an illustrative approach to detecting distinct labels subsequent to hybridization to the sample's genetic DNA.

Referring now to FIG. 2(A-D), shown is a schematic of an illustrative approach to analyzing a sample for a chromosomal translocation associated with a breakpoint. A breakpoint region 27 is depicted as being spanned by a first nucleic acid probe 21, a second nucleic acid probe 23, and a third nucleic acid probe 22. The nucleic acid probes are labeled, a first label shown as diamond 221, a second label shown as a triangle 222, and a third label 223 shown as a pentagon. While the probes are shown with a single label, this representation is merely symbolic. Each probe would actually be labeled with a plurality of labels. For example, the first nucleic acid probe 21 may include a 700 kb nucleic acid sequence nick translated to a multiplicity of smaller haptenated oligonucleotide probe species. Exemplary locations for a breakpoint are shown as arrows 24, 25, and 26. FIG. 2(A-D) show an illustrative method for analyzing a sample comprising (A) contacting the sample with at least three probes and establishing conditions appropriate for hybridization of those probes with the genetic DNA found in the sample, (B) contacting the sample with an antibody 28 directed towards one of the labeled probes, (C) contacting the sample with a second antibody 29 conjugated to a plurality of enzyme molecules, and (D) contacting the sample with a detection reagent that results in the deposition of a detectable species 19 proximally to the probe using enzymatic deposition.

Referring again to FIG. 2A, in an illustrative embodiment, contacting the sample with a first nucleic acid probe includes a first nucleic acid probe 21 having a first sequence configured to hybridize to genomic DNA located 5' to the breakpoint. Three potential breakpoints are shown by arrows 24, 25, and 26. Regardless of which breakpoint position is selected, probe 21 remains 5' of the breakpoint. Similarly, a second nucleic acid probe 23 having a second sequence configured to hybridize to genomic DNA located 3' to the breakpoint is shown in a location 3' to each of the breakpoint positions. The method for analyzing a sample comprises contacting the sample with a third nucleic acid probe comprising a third sequence configured to hybridize to genomic DNA adjacent to the breakpoint. An exemplary sequence configured to hybridize to genomic DNA adjacent to the breakpoint is shown as probe 22. As indicated by exemplary breakpoints 24, 25, and 26, probe 22 is either adjacent to the breakpoint by its position directly to one side or the other (e.g. shown by arrows 24 or 26) or by spanning the breakpoint (arrow 25).

Referring now to FIG. 2B, shown is a representation of the illustrative step of contacting the sample with an antibody 28 directed towards one of the labeled probes. For example, a hapten-labeled probe may be detected by contacting the sample with an anti-hapten antibody. FIG. 2(A-D) show an exemplary hybridization of three probes and subsequent detection of one of those probes. Sequential or concurrent detection strategies could be used to detect hybridization of the other probes. That is, additional antibodies specific to label 222 and label 223 could be contacted to the sample simultaneously or sequentially to antibody 28. Furthermore, the step represented by FIG. 2C of contacting the sample with a second antibody 29 conjugated to a plurality of enzyme molecules may be accompanied simultaneously or sequentially with like steps to detect label 222 and label 223. In the same manner, the detection step represented by FIG. 2D may be accompanied simultaneously or sequentially with like steps to deposit additional detectable species corresponding to label 222 and label 223. Illustratively, the detectable species for labeling each of the labels is distinct.

Referring to FIG. 1, probes 121, 122, and 123 are shown with distinct patterns. Similarly, with reference to FIG. 2A-2D, labels 221, 222, and 223 are shown with distinct shapes. The use of distinct patterns and shapes is intended to indicate that diverse detection strategies can be used for the detection of these various probes. As such, detection chemistries can be selected that allow for the differentiation of the location of the various probes. In illustrative embodiments, detecting hybridization of the probes includes detecting a first signal associated with the first nucleic acid probe, a second signal associated with the second nucleic acid probe, and a third signal associated with the third nucleic acid probe. In one embodiment, the signals are distinct. In some preferred embodiments, the first, second and third probes are labeled with different detectable moieties, such as haptens, which allow hybridization of each of the three probes to be resolved.

In some embodiments of the present disclosure, the systems comprise a first nucleic acid probe set that hybridizes to a portion of the genomic DNA that is 5' to a chromosomal breakpoint (i.e., a first defined area of the genomic DNA), a second nucleic acid probe set that hybridizes to a portion of the genomic DNA that is 3' to the chromosomal breakpoint (i.e., a second defined area of the genomic DNA), and a third nucleic acid probe set comprising a 5' portion and a 3' portion and which hybridizes to 5' and 3' sequences adjacent to the chromosomal breakpoint region so that the third nucleic acid probe spans (i.e., hybridizes to a defined region spanning) the chromosomal breakpoint region in the absence of a rearrangement (i.e., a third defined area of the genomic DNA). It will be appreciated that the probe set to the breakpoint region comprises a portion of individual probes that hybridize to the genomic DNA 5' to the breakpoint (i.e., 5' hybridizing portion) and a portion of individual probes that hybridize to the genomic DNA 3' to the breakpoint (i.e., 3' hybridizing portion). In embodiments where the breakpoint is within a gene, the systems may comprise a first nucleic acid probe that hybridizes to a 5' noncoding region of a target sequence, a second nucleic acid probe that hybridizes to 3' noncoding region of a target sequence, and a third nucleic acid probe comprising a 5' portion and a 3' portion and which hybridizes to 5' and 3' sequences adjacent to the breakpoint of the target sequence so that the third nucleic acid probe spans (i.e., hybridizes to a defined region spanning) across the breakpoint of the target sequence when the target sequence is not rearranged.

In illustrative embodiments, the method of analyzing a sample includes detection of a translocation. Referring now to FIG. 3, shown is a translocation that occurs on the same chromosome (e.g. EML4-ALK fusion gene). Referring now to FIG. 7, shown is a translocation that occurs between different chromosomes (e.g. KIF5B-ALK fusion or TFG-ALK fusion). Referring again to FIG. 3, shown is an exemplary method and application of a system for analyzing a sample for a chromosomal translocation associated with a breakpoint. Shown is a representation of Chromosome 2 10, a breakpoint region associated with the ALK gene 20, and a breakpoint associated with the EML4 gene 30. For the EML4 and ALK genes, a distance 11 between the genes is about 12 Mb, ALK being located at 2p23 and EML4 being located at 2p21. Across the breakpoint region associated with the ALK gene 20, three probes have been configured to have sequences complimentary to unique regions of the ALK gene. A first probe 321 is complimentary to a sequence 3' to the breakpoint, a second probe 323 is complementary to a sequence 5' to the breakpoint, and a third probe 322 is complimentary to a sequence spanning the breakpoint. Chromosome 2 10 is shown in FIG. 3 in its wild-type without a translocation. FIG. 4 shows Chromosome 2 410 that includes an inversion associated with the ALK-EML4 fusion gene. The impact of the inversion on the localization of the probes is indicated by the localization of probes 321, 322, and 323. That is, the chromosomal translocation can be identified by the distinct manner in which the probes hybridize to the genetic DNA. Referring now to FIG. 5(A-B), shown are schematics showing the manner in which a chromosomal spread 500 having a wild-type gene configuration (FIG. 5A) could be distinguished from a chromosomal spread 501 having an ALK-EML4 fusion gene (FIG. 5B) according to a method described herein. In particular, FIG. 5A corresponds to the schematic shown in FIG. 3; the sequence of the labeling is in the order of 321, 322, and 323. Referring now to FIG. 6A, shown is an embodiment where probe 321 was detected with red chromogen, probe 322 was detected with blue chromogen, and probe 323 was detected with yellow chromogen. Accordingly, as shown pictorially in FIG. 6A and schematically in FIG. 5A, the order and orientation of the probes generates a signal having an order and orientation of red, blue, and yellow aligned longitudinally along the length of the chromosome. In FIG. 6A, the red, blue, and yellow signals are indicated with arrows marked with "R" (red signal), "B" (blue signal) or "Y" (yellow signal). Similarly, FIG. 5B corresponds to the schematic shown in FIG. 4; the sequence of the labeling is in the order of 321, 322, 323, and 322 arranged in two separate clusters. Referring now to FIG. 6B, shown is an embodiment where probe 321 was detected with red chromogen, probe 322 was detected with blue chromogen, and probe 323 was detected with yellow chromogen. Accordingly, as shown pictorially in FIG. 6B and schematically in FIG. 5B, the order of the probes generates a signal having an order and orientation of red, blue, yellow, and blue arranged in two clusters of signals, one comprising red and blue and the other comprising yellow and blue. In FIG. 6B, the red, blue, and yellow signals are indicated with arrows marked with "R" (red signal), "B" (blue signal) or "Y" (yellow signal). In FIG. 5B, it can be seen that one copy of the gene remains in the wild-type configuration, but the second copy of the gene shows an inversion ISH signal. The inversion ISH signal includes a split of probe 322 that spans the breakpoint so that two signals (shown as blue or as the black dot in FIGS. 6B and 5B respectively). The signals from the split probe may be of diminished intensity due to the fact that the same length of probe is localized in two places. In a wild-type chromosome, the probes are configured to be in close proximity to each other on a chromosome resulting in tightly clustered ISH signals. This can be seen clearly in FIG. 5A. For a chromosome that includes a translocation, the ISH signals exhibit a spread as shown in FIG. 5B as double arrow 510.

Figure 8:
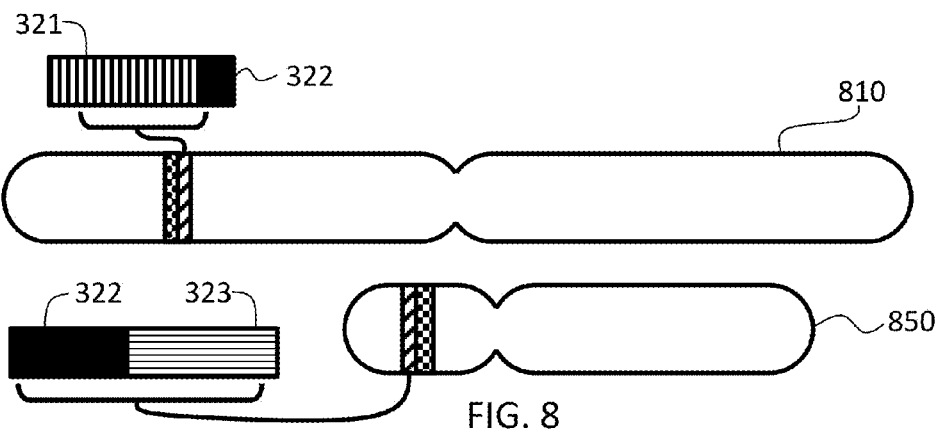
FIG. 8 is a schematic depiction showing the chromosome of FIG. 7 subsequent to the rearrangement chromosomal translocation and the resulting localization of the probes.
Figures 9A, 9B:
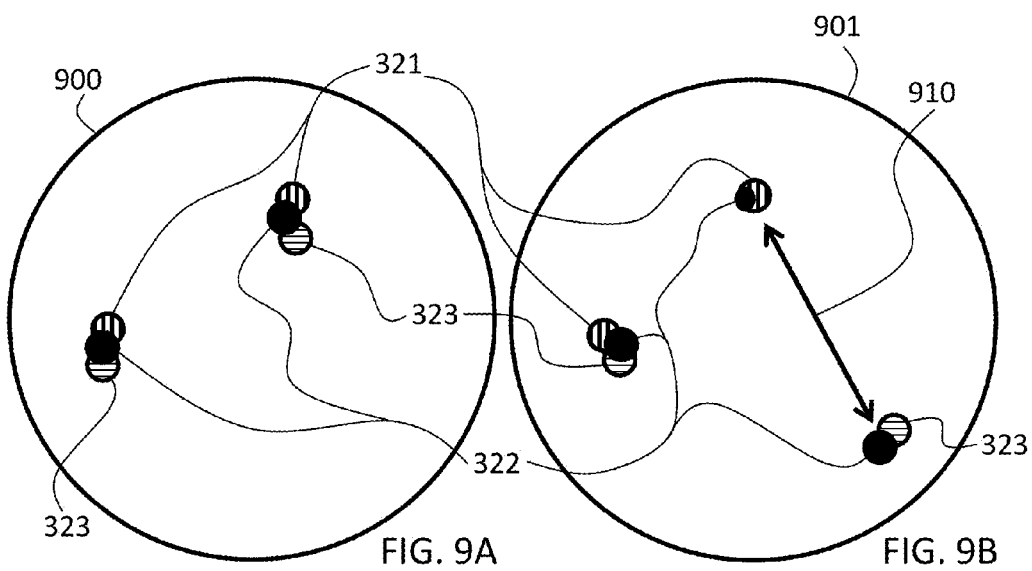
FIG. 9(A-B) is a magnified top plan view showing the signal reported for (A) wild-type ALK and (B) rearranged ALK as would be seen using triple colorimetric detection and bright-field imaging.

In one embodiment, the method of analyzing a sample includes detection of a translocation. Referring now to FIG. 7, shown is a translocation that occurs between different chromosomes (e.g. KIF5B-ALK fusion or TFG-ALK fusion). Shown is a representation of Chromosome 2 10, a breakpoint region associated with the ALK gene 20, and a representation of Chromosome 10 50 and breakpoint associated with the KIF5B gene 52. According to this translocation, region 12 of Chromosome 2 10 translocates with region 512 of Chromosome 10 50 according to the arrow 55. This translocation results in the modified chromosomes shown in FIG. 8, modified Chromosome 2 810 and modified Chromosome 10 850. Across the breakpoint region associated with the ALK gene 20, three probes having sequences complimentary to unique regions of the ALK gene have been designed. A first probe 321 is complimentary to a sequence 3' to the breakpoint, a second probe 323 is complimentary to a sequence 5' to the breakpoint, and a third probe 322 is complementary to a sequence spanning the breakpoint. These probes, spanning the breakpoint region associated with the ALK gene 20, are shown in FIG. 3. Referring now to FIG. 9(A-B), schematics representing the manner in which a chromosomal spread 900 having a wild-type gene configuration (FIG. 9A) may be distinguished from a chromosomal spread 901 having a KIF5B-ALK fusion gene (FIG. 9B) according to a method described herein. In particular, FIG. 9A corresponds to the schematic shown in FIG. 7; the sequence of the labeling is in the order and orientation of 321, 322, and 323 arranged longitudinally along the length of the chromosome in a tightly distributed cluster. As shown schematically in FIG. 9A, the order of the probes generates a signal having a first order (e.g. red, black, and blue). Similarly, FIG. 9B corresponds to the schematic shown in FIG. 8; the sequence of the labeling is in the order and orientation of 321, 322, 323, and 322 (e.g. red-black separated from blue-black). In FIG. 9B, it can be seen that one copy of the gene remains in the wild-type configuration, but the second copy of the gene shows a translocated ISH signal. The translocated ISH signal includes a split of probe 322 that spans the breakpoint so that two signals (shown as the black dots in FIG. 9B) are separated by a substantial distance, represented by double-arrow 910. The signals from the split probe may be of diminished intensity due to the fact that the same length of probe is localized in two places. The distance between the signals shown in FIG. 9B, when contrasted to the clustered signals shown in FIG. 9A, provides evidence that the fusion gene is present.

In illustrative embodiments, a method according to the present disclosure includes detecting hybridization of the probes by detecting a first signal associated with the first nucleic acid probe, a second signal associated with the second nucleic acid probe, and a third signal associated with the third nucleic acid probe. As shown in FIGS. 5(A-B) and 9(A-B), when a chromosomal rearrangement has occurred, a signal is generated where a signal (e.g., a colorimetric signal, fluorometric signal or luminescent signal from an appropriate label as described in more detail below) from the third nucleic acid probe separately co-localizes with each of the signals from the first and second nucleic acid probes. As can be seen, there is a distinct first signal comprising a signal from the first nucleic acid probe and a signal from the third nucleic probe and a distinct second signal comprising a signal from the second nucleic acid probe and signal from the third nucleic acid probe. The first and second distinct signals can be located on genomic DNA belonging to the same or different chromosomes depending on the rearrangement. In samples where rearrangement has occurred, the probe set corresponding to the breakpoint region is split, with separate portions of the probe set hybridizing to the 5' and 3' regions flanking the breakpoint, i.e., the 5' hybridizing portion of the probe set hybridizes to the 5' end of the rearranged target sequence and the 3' hybridizing portion of the probe set hybridizes to the 3' portion of the rearranged target sequence. This hybridization pattern leads to a split (i.e., two separate signals) for the third probe. When the third probe is labeled with a separate color from the first two probes, the resolution of the assay and the ability to distinguish false positive signals is greatly enhanced.

As also shown in FIGS. 5(A-B) and 9(A-B), when a chromosomal translocation has not occurred, a signal is generated where a signal (e.g., a colorimetric signal, fluorometric signal or luminescent signal from an appropriate label as described in more detail below) from the third nucleic acid probe co-localizes with each of the signals from the first and second nucleic acid probes. As can be seen, there is a single signal comprising signals from the first, second and third nucleic acids. In this situation, the first and second probes hybridize to the 5' and 3' regions of the target sequence and the third probe hybridizes to the target sequence such that it spans (i.e., hybridizes to a region spanning) the presumptive breakpoint.

In some embodiments of the present disclosure, the systems comprise a first nucleic acid probe set that hybridizes to a portion of the genomic DNA that is 5' to a chromosomal breakpoint (i.e., a first defined area of the genomic DNA), a second nucleic acid probe set that hybridizes to a portion of the genomic DNA that is 3' to the chromosomal breakpoint (i.e., a second defined area of the genomic DNA), and a third nucleic acid probe set that hybridizes to an area of genomic immediately 5' to the chromosomal breakpoint region in the absence of a rearrangement (i.e., a third defined area of the genomic DNA), and in preferred embodiments, hybridizes to a target rearranged gene (e.g., ALK as depicted in FIG. 3). In alternative embodiments, the third nucleic acid probe set hybridizes to an area of genomic immediately 3' to the chromosomal breakpoint region in the absence of a rearrangement (i.e., a third defined area of the genomic DNA), and in preferred embodiments, hybridizes to a target rearranged gene. In some preferred embodiments, the first, second and third probes are labeled with different detectable moieties, such as haptens, which allows hybridization of each of the three probes to be resolved. For example, when a chromosomal rearrangement has occurred, a signal is generated where a signal (e.g., a colorimetric signal, fluorometric signal or luminescent signal from an appropriate label as described in more detail herein) from the third nucleic acid probe separately co-localizes with the signal from the 5' probe in a changed orientation as compared to the non-rearranged genomic DNA. In preferred embodiments, the changed orientation is an inverted orientation as depicted, for example, in FIG. 5B. As used herein, the term inverted when used in reference to a probe hybridization patter refers to an orientation which is the opposite of that observed in a wild-type sample. In alternative embodiments, where the third probe set hybridizes to an area of genomic immediately 3' to the chromosomal breakpoint region in the absence of a rearrangement, the signal from the third probe set co-localizes with the 3' probe.

In some embodiments, the first, second and third nucleic acid probes comprise a detectable moiety. In some embodiments, the detectable moiety is selected from the group consisting of a hapten, an enzyme, a fluorescent molecule, a luminescent molecule and a radioactive molecule. In some embodiments, the detectable moiety is a hapten, and the first, second and third nucleic acid probes are labeled with different first, second and third haptens, respectively. In some embodiments, the different first, second and third haptens are selected from the group consisting of biotin, 2,4-Dintropheyl (DNP), Fluorescein deratives, Digoxygenin (DIG), 5-Nitro-3-pyrozolecarbamide (nitropyrazole, NP), 4,5,-Dimethoxy-2-nitrocinnamide (nitrocinnamide, NCA), 2-(3,4-Dimethoxyphenyl)-quinoline-4-carbamide (phenylquinolone, DPQ), 2,1,3-Benzoxadiazole-5-carbamide (benzofurazan, BF), 3-Hydroxy-2-quinoxalinecarbamide (hydroxyquinoxaline, HQ), 4-(Dimethylamino)azobenzene-4'-sulfonamide (DABSYL), Rotenone isoxazoline (Rot), (E)-2-(2-(2-oxo-2,3-dihydro-1H-benzo[b][1,4]diazepin-4-yl)phenozy)acetamide (benzodiazepine, BD), 7-(diethylamino)-2-oxo-2H-chromene-3-carboxylic acid (coumarin 343, CDO), 2-Acetamido-4-methyl-5-thiazolesulfonamide (thiazolesulfonamide, TS), and p-Mehtoxyphenylpyrazopodophyllamide (Podo). In some embodiments, the detecting further comprises contacting the sample with first, second and/or third antibodies specific for the first, second and third haptens, respectively. In some embodiments, the first, second and third antibodies are conjugated to an enzyme. In some embodiments, the enzyme is selected from the group consisting of horseradish peroxidase, alkaline phosphatase, acid phosphatase, glucose oxidase, β-galactosidase, β-glucuronidase and β-lactamase. In some embodiments, the methods further comprise contacting the sample with antibodies that bind to the first, second, and/or third antibodies. In some embodiments, the antibodies that bind to the first, second and/or third antibodies are conjugated to an enzyme. In some embodiments, the enzyme is selected from the group consisting of horseradish peroxidase, alkaline phosphatase, acid phosphatase, glucose oxidase, β-galactosidase, β-glucuronidase and β-lactamase. In some embodiments, the antibodies that bind to the first, second and/or third antibodies are conjugated to different fluorescent molecules.

In some embodiments, the methods further comprise contacting the sample with colorimetric detection reagents. In some embodiments, the methods further comprise contacting the sample with colorimetric detection reagents. In some embodiments, the detecting comprises a process selected from the group consisting of colorimetric detection, fluorometric detection, and radiometric detection. In some embodiments, the presence of a chromosomal translocation is indicated by hybridization of the first nucleic acid probe portion to the genomic DNA that is located 5' to the breakpoint, hybridization of the second nucleic acid probe portion to the genomic DNA that is located 3' to the breakpoint, and the separate hybridization of the 5' portion of the third nucleic acid probe to the 5' sequence adjacent to the breakpoint and the 3' portion of the third nucleic acid probe to the 3' sequence adjacent to the breakpoint. In some embodiments, the absence of a chromosomal translocation is indicated by hybridization of the first nucleic acid probe portion to the genomic DNA that is located 5' to the breakpoint, hybridization of the second nucleic acid probe portion to the genomic DNA that is located 3' to the breakpoint, and the hybridization of the 5' portion of the third nucleic acid probe to the 5' sequence adjacent to the breakpoint and the 3' portion of the third nucleic acid probe to the 3' sequence adjacent to the breakpoint so that the third probes hybridize to a region of the genomic DNA spanning the breakpoint.

In some embodiments, the present disclosure provides systems for analyzing a sample suspected of having a chromosomal translocation associated with a breakpoint comprising: a first nucleic acid probe that hybridizes to a portion of the genomic DNA that is located 5' to the breakpoint, a second nucleic acid probe that hybridizes to a portion of the genomic DNA that is located 3' to the breakpoint, and a third nucleic acid probe that hybridizes to a portion of DNA that is adjacent to the breakpoint. In some embodiments, the third nucleic acid probe further comprises a 5' portion and 3' portion, wherein the 5' portion hybridizes to a portion of the genomic DNA that is 5' and adjacent to the breakpoint and the 3' portion hybridizes to a portion of the genomic DNA that is 3' and adjacent to the breakpoint so that the third nucleic acid probe hybridizes to a region of the genomic DNA spanning the breakpoint in the absence of a rearrangement. In some embodiments, the third nucleic acid probe hybridizes to a portion of genomic DNA that is 5' and adjacent to the breakpoint so that in the presence of a rearrangement a signal detected for the first nucleic acid probe and a signal detected for the third nucleic acid probe have an orientation which is inverted as compared to the orientation of the signal detected for the first nucleic acid probe and the signal detected for the third nucleic acid probe in the absence of a rearrangement. In some embodiments, the third nucleic acid probe hybridizes to a portion of genomic DNA that is 3' and adjacent to the breakpoint so that in the presence of a rearrangement a signal detected for the second nucleic acid probe and a signal detected for the third nucleic acid probe have an orientation which is inverted as compared to the orientation of the signal detected for the second nucleic acid probe and the signal detected for the third nucleic acid probe in the absence of a rearrangement.

In some embodiments, the present provides kits for analyzing a sample suspected of having a chromosomal translocation associated with a breakpoint comprising: a first nucleic acid probe that hybridizes to a portion of the genomic DNA that is located 5' to the breakpoint, a second nucleic acid probe that hybridizes to a portion of the genomic DNA that is located 3' to the breakpoint, and a third nucleic acid probe that hybridizes to a portion of DNA that is adjacent to the breakpoint. In some embodiments, the third nucleic acid probe further comprises a 5' portion and 3' portion, wherein the 5' portion hybridizes to a portion of the genomic DNA that is 5' and adjacent to the breakpoint and the 3' portion hybridizes to a portion of the genomic DNA that is 3' and adjacent to the breakpoint so that the third nucleic acid probe hybridizes to a region of the genomic DNA spanning the breakpoint in the absence of a rearrangement. In some embodiments, the third nucleic acid probe hybridizes to a portion of genomic DNA that is 5' and adjacent to the breakpoint so that in the presence of a rearrangement a signal detected for the first nucleic acid probe and a signal detected for the third nucleic acid probe have an orientation which is inverted as compared to the orientation of the signal detected for the first nucleic acid probe and the signal detected for the third nucleic acid probe in the absence of a rearrangement. In some embodiments, the third nucleic acid probe hybridizes to a portion of genomic DNA that is 3' and adjacent to the breakpoint so that in the presence of a rearrangement a signal detected for the second nucleic acid probe and a signal detected for the third nucleic acid probe have an orientation which is inverted as compared to the orientation of the signal detected for the second nucleic acid probe and the signal detected for the third nucleic acid probe in the absence of a rearrangement.

In some embodiments, the present disclosure provides methods for diagnosing a disease associated with a chromosomal translocation associated with a breakpoint comprising:

providing a sample from a patient suspected of having a disease associated with a chromosomal translocation associated with a breakpoint and providing a first nucleic acid probe that hybridizes to a portion of the genomic DNA that is located 5' to the breakpoint, a second nucleic acid probe that hybridizes to a portion of the genomic DNA that is located 3' to the breakpoint, and a third nucleic acid probe that hybridizes to a portion of DNA that is adjacent to the breakpoint; hybridizing the probes to genomic DNA in the sample; detecting hybridization of the probes to the genomic DNA in the sample; using results from the detection to provide a diagnosis of the disease in the patient.

In some embodiments, the present disclosure provides methods for predicting the outcome for a patient suffering from a disease associated with a chromosomal translocation associated with a breakpoint comprising: providing a sample from a patient suspected of having a disease associated with a chromosomal translocation associated with a breakpoint and providing a first nucleic acid probe that hybridizes to a portion of the genomic DNA that is located 5' to the breakpoint, a second nucleic acid probe that hybridizes to a portion of the genomic DNA that is located 3' to the breakpoint, and a third nucleic acid probe that hybridizes to a portion of DNA that is adjacent to the breakpoint; hybridizing the probes to genomic DNA in the sample; detecting hybridization of the probes to the genomic DNA in the sample; and using results from the detection to provide a prognosis related to the disease in the patient.

In some embodiments, the present disclosure provides methods of determining a therapy for patients suffering from a disease associated with a chromosomal translocation associated with a breakpoint comprising: providing a sample from a patient suspected of having a disease associated with a chromosomal translocation associated with a breakpoint and providing a first nucleic acid probe that hybridizes to a portion of the genomic DNA that is located 5' to the breakpoint, a second nucleic acid probe that hybridizes to a portion of the genomic DNA that is 3' to the breakpoint, and a third nucleic acid probe that hybridizes to a portion of DNA that is adjacent to the breakpoint; hybridizing the probes to genomic DNA in the sample; detecting hybridization of the probes to the genomic DNA in the sample; and using results from the detection to determine a therapeutic treatment for the patient.

In previously described two-color break-apart probe systems, there has been a problem due to the gap between 5' and 3' break-apart probes. Dependent on how 5' and 3' probe signals are angled within a cell, 5' and 3' probe signals can be seen as 2 separate probe signals even though no rearrangement has occurred. This is a false positive signal. The current system resolves these problems by introducing a third probe that generates a signal in conjunction with the first two probes. This system is especially useful where the rearrangement occurs with the same chromosome (e.g., an inversion) although the system also has the advantage of generating easy to read signals when the translocation occurs between chromosomes. Various embodiments are described in more detail below.

A. Target Nucleic Acid Probes

The present disclosure utilizes nucleic acid probes. In preferred embodiments, the nucleic acid probe is a probe set that binds or hybridizes to a defined area of a genomic DNA (i.e, the target nucleic acid sequence) in a sample as described above. Preferably, the nucleic acid probe comprises any suitable nucleic acid, such as RNA (Ribonucleic acid), DNA (Deoxyribonucleic acid), LNA (Locked Nucleic Acid), PNA (Peptide Nucleic Acid) or combinations thereof, and can comprise both standard nucleotides such as ribonucleotides and deoxyribonucleotides and nucleotide analogs.

In some embodiments, the nucleic acid probe set is greater than 80% complementary to the desired target nucleic acid sequence, preferably greater than 90% complementary to the desired target nucleic acid sequence, more preferably greater than 99% complementary to the desired target nucleic acid sequence, and most preferably about 100% complementary to the desired target nucleic acid sequence. In general, design of the nucleic acid probe is accomplished using practices that are standard in the art. For example, sequences that have self complementarity, such that the resulting probes would either fold upon themselves, or hybridize to each other at the expense of binding to the target nucleic acid, are generally avoided.

One consideration in choosing a length for the target probe portion is the complexity of the sample containing the target nucleic acid. For example, the human genome is approximately $3 \times 10^9$ base pairs in length. Any 10-nucleotide sequence will appear with a frequency of approximately 2,861 times in 3 billion base pairs. A target probe portion of this length would have a poor chance of binding uniquely to a 10 nucleotide region within a target having a sequence the size of the human genome. If the target sequence were within a 3 kb plasmid, however, such an oligonucleotide might have a very reasonable chance of binding uniquely. By this same calculation it can be seen that an oligonucleotide of 16 nucleotides (i.e., a 16-mer) is the minimum length of a sequence that is mathematically likely to appear once in $3 \times 10^9$ base pairs. This level of specificity may also be provided by two or more shorter nucleic acid sequences if they are configured to bind in a cooperative fashion (i.e., such that they can produce the intended complex only if both or all are bound to their intended target sequences), wherein the combination of the short sequences provides the desired specificity.

A second consideration in choosing target probe portion length is the temperature range in which the target probe portion will be expected to function. A 16-mer of average base content (50% G-C bases) will have a calculated $T_m$ of about 41° C., depending on, among other things, the concentration of the probe and its target, the salt content of the reaction and the precise order of the nucleotides. As a practical matter, longer target probe portions are usually chosen to enhance the specificity of hybridization. For example, target probe portions of from 20 to 25 nucleotides in length can be used, as they are highly likely to be specific if used in reactions conducted at temperatures which are near their $T_m$s (within about 5° C. of the $T_m$).

In preferred embodiments, the nucleic acid probe set is designed taking these considerations into account, so that the target probe portion will hybridize to a target nucleic acid under suitable conditions defined by the user.

The nucleic acid can be selected manually, or with the assistance of a computer implemented algorithm that optimizes primer selection based on desired parameters, such as temperature, length, GC content, etc. Numerous computer implemented algorithms or programs for use via the internet or on a personal computer are available. For example, to generate multiple binding regions from a target nucleic acid sequence (e.g., genomic target nucleic acid sequence), regions of sequence devoid of repetitive (or other undesirable, e.g., background-producing) nucleic acid sequence are identified, for example manually or by using a computer algorithm. Within a target nucleic acid sequence (e.g., genomic target nucleic acid sequence) that spans several to several-hundred kilobases, typically numerous binding regions that are substantially or completely free of repetitive (or other undesirable, e.g., background-producing) nucleic acid sequences are identified.

The nucleic acid probes can be synthesized by any known method. In some embodiments, the sequences encoding the nucleic acid probes are cloned into a plasmid expression vector. The nucleic probe is preferably transcribed from the vector with an RNA polymerase to provide an RNA molecule encoding the nucleic acid probe. In some embodiments, the nucleic acid probe is chemically synthesized, for example, using phosphoramidite analogs. In some embodiments, DNA probes are synthesized by propagation, purification and restriction digestion of plasmid DNA to provide a DNA molecule encoding the target nucleic acid probe. The double stranded DNA can be subsequently melted into single strands for use in hybridization protocols. In some embodiments, the target nucleic acid probes are synthesized by asymmetric PCR. In some embodiments, one primer, could for example, be a nucleic acid analog (e.g., LNA). This process generates a probe with the target specific portion containing locked nucleotides and the detection target portion being made from standard dNTP's. In some embodiments, the LNA containing primer contains a biotin to facilitate purification of the desired strand.

In some embodiments, the nucleic acid probes comprise one or detectable moieties. In some embodiments, the detectable moieties are directly detectable, while in other embodiments, the detectable moieties are indirectly detectable. In some embodiments, the detectable moieties are incorporated into the detection probe. In some embodiments, the detectable moieties are signal generating moieties that produce a detectable signal. In some embodiments, the detectable moiety is conjugated to nucleotides or nucleotide analogs used in the synthesis of the detection probe. For example, nucleoside phosphoramidites that are conjugated to a desired detectable moiety are used to synthesize a detection probe via chemical synthesis as is known in the art.

In some embodiments, the detectable moiety is detected indirectly. In some embodiments, the detectable moiety is a first member of a binding molecule system that includes first and second or first second and third members. In these embodiments, nucleotides conjugated to a first member of a binding pair are incorporated into the detection probe, preferably via the use nucleoside phosphoramidites conjugated to the first member of the binding pair. The sample is then contacted with a specific binding agent comprising the second member of the binding pair (i.e., a specific binding moiety). In some embodiments, the second member of the binding pair is conjugated to a signal generating moiety and used detect the detection probe via binding to the first member of the binding pair. In other embodiments, the sample is contacted with a third binding member which binds to the second binding member. In these embodiments, the third binding member is conjugated to a signal generating moiety. Examples of suitable binding molecule systems include, but are not limited to, avidin, biotin, haptens, anti-hapten antibodies, and anti-antibody antibodies, and combinations thereof. For example, in some embodiments, the detectable moiety portion of the detection probe comprises one or more haptenylated nucleotides. These haptenylated nucleotides are detected by the use of an antihapten antibody and an anti-(antihapten antibody) antibody that is conjugated to a signal generating moiety.

Accordingly, in some embodiments, the present disclosure provides nucleic acid probes that comprise one or more nucleotides that are conjugated to the first member of a binding molecule system. In some embodiments, the first member of the binding molecule system is a hapten. In some embodiments, the detectable moiety portion of the detection probe is a nucleic acid molecule that incorporates dNTPs covalently attached to hapten molecules (such as a nitroaromatic compound (e.g., dinitrophenyl (DNP)), biotin, fluorescein, digoxigenin, etc.). Methods for conjugating haptens and other labels to dNTPs (e.g., to facilitate incorporation into labeled probes) are well known in the art. For examples of procedures, see, e.g., U.S. Pat. Nos. 5,258,507, 4,772,691, 5,328,824, and 4,711,955. Indeed, numerous labeled dNTPs are available commercially, for example from Invitrogen Detection Technologies (Molecular Probes, Eugene, Oreg.). A label can be directly or indirectly attached of a dNTP at any location on the dNTP, such as a phosphate (e.g., $\alpha$, $\beta$ or $\gamma$ phosphate) or a sugar.

A variety of haptens may be used in the nucleic acid probe. Such haptens include, but are not limited to, pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof. Specific examples of haptens include, but are not limited to, 2,4-Dintropheyl (DNP), Biotin, Fluorescein deratives (FITC, TAMRA, Texas Red, etc.), Digoxygenin (DIG), 5-Nitro-3-pyrozolecarbamide (nitropyrazole, NP), 4,5,-Dimethoxy-2-nitrocinnamide (nitrocinnamide, NCA), 2-(3,4-Dimethoxyphenyl)-quinoline-4-carbamide (phenylquinolone, DPQ), 2,1,3-Benzoxadiazole-5-carbamide (benzofurazan, BF), 3-Hydroxy-2-quinoxalinecarbamide (hydroxyquinoxaline, HQ), 4-(Dimethylamino)azobenzene-4'-sulfonamide (DABSYL), Rotenone isoxazoline (Rot), (E)-2-(2-(2-oxo-2,3-dihydro-1H-benzo[b][1,4]diazepin-4-yl)phenozy)acetamide (benzodiazepine, BD), 7-(diethylamino)-2-oxo-2H-chromene-3-carboxylic acid (coumarin 343, CDO), 2-Acetamido-4-methyl-5-thiazolesulfonamide (thiazolesulfonamide, TS), and p-Mehtoxyphenylpyrazopodophyllamide (Podo). These haptens and their use in probes are described in more detail in co-owned applications US Pat. Publ. Nos. 2008/0305497, 2008/0268462, and 2008/0057513, incorporated herein by reference in their entirety.

In embodiments where the nucleic acid probe comprises haptens, the second member of the binding molecule system is preferably a molecule that binds to the hapten such as an antigen binding molecule. Examples of suitable antigen binding molecules include, but are not limited to, antibodies, immunoglobulins or immunoglobulin-like molecules (including by way of example and without limitation, IgA, IgD, IgE, IgG and IgM), antibody fragments such as F(ab')$_2$ fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'$_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079-5,874,541; 5,840,526; 5,800, 988; and 5,759,808). In some embodiments, a detectable moiety that generates a detectable signal is attached, covalently or otherwise, to the antigen binding molecule. Examples of suitable second binding pair members include, but are not limited to anti-DNP, anti-biotin, anti-FITC, anti-DIG, anti-NP, anti-NCA, anti-DPQ, anti-BF, anti-HQ, anti-DABSYL, anti-Rot, anti-BD, anti-CDO, anti-TS, and anti-Podo antibodies that are conjugated to a detectable moiety that generates a detectable signal. In further embodiments, second member of the binding molecule system is an anti-hapten primary antibody that does not comprise a detectable moiety. In these embodiments, the third member of the binding molecule system is a secondary anti-antibody (such as a goat anti-mouse IgG antibody) that comprises a detectable moiety that generates a signal is utilized for generating a detectable signal.

As described above, the detection probe can be directly detectable or indirectly detectable. In some direct detection embodiments, the detection probe comprises detectable moieties (e.g., signal generating moieties) that generate a detectable signal, while in some indirect detection embodiments, a specific binding agent comprising a member of a binding molecule system (such as a secondary antibody) that is conjugated to a signal generating moiety that generates a detectable signal is utilized. In these embodiments, a variety of signal generating moieties that generate a detectable signal may be incorporated into the detection probe or conjugated to the member of the binding pair.

In preferred embodiments, the signal generating moiety can be detected by any known or yet to be a discovered mechanism including absorption, emission and/or scattering of a photon (including radio frequency, microwave frequency, infrared frequency, visible frequency and ultraviolet frequency photons). Signal-generating moieties include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), and paramagnetic and magnetic molecules or materials.

Particular examples of signal-generating moieties include fluorescent molecules (or fluorochromes). Numerous fluorochromes are known to those of skill in the art, and can be selected, for example from Invitrogen, e.g., see, The Handbook—A Guide to Fluorescent Probes and Labeling Technologies, Invitrogen Detection Technologies, Molecular Probes, Eugene, Oreg.). Examples of particular fluorophores that can be attached (for example, chemically conjugated) to a nucleic acid molecule or protein such as an antigen binding molecule include, but are not limited to, 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS),4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2',7'-difluorofluorescein (OREGON GREEN™); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Invitrogen Detection Technologies, Molecular Probes (Eugene, Oreg.) and including the ALEXA FLUOR™ series of dyes (for example, as described in U.S. Pat. Nos. 5,696,157, 6,130,101 and 6,716,979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, (e.g. QDOT NANOCRYSTALS, Life Technologies; see also, U.S. Pat. Nos. 6,815, 064, 6,682,596 and 6,649,138). Semiconductor nanocrystals are microscopic particles having size-dependent optical and/ or electrical properties. When semiconductor nanocrystals are illuminated with a primary energy source, a secondary emission of energy occurs of a frequency that corresponds to the band-gap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et. al. (1998) Science 281:2013-6, Chan et al. (1998) Science 281:2016-8, and U.S. Pat. No. 6,274,323.

Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, semi-conductor nanocrystals that emit light at different wavelengths based on size (565 nm, 655 nm, 705 nm, or 800 nm emission wavelengths), which are suitable as fluorescent labels in the probes disclosed herein are available from Invitrogen.

Additional signal-generating moieties include, for example, radioisotopes (such as $^3$H, $^{35}$S and $^{32}$P), metal chelates such as DOTA and DPTA chelates of radioactive or paramagnetic metal ions like $Gd^{3+}$, and liposomes.

Signal-generating moieties also include enzymes, for example horseradish peroxidase, alkaline phosphatase, acid phosphatase, glucose oxidase, β-galactosidase, β-glucuronidase or β-lactamase. Where the detectable label includes an enzyme, a chromogen, fluorogenic compound, or luminogenic compound can be used in combination with the enzyme to generate a detectable signal (numerous of such compounds are commercially available, for example, from Life Technologies). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-.beta.-D-galactopyranoside (MU-Gal), p-nitrophenyl-α-D-galactopyranoside (PNP), 5-bromo-4-chloro-3-indolyl-.beta.-D-glucuronide (X-Gluc), 3-amino-9-ethyl carbazol (AEC), fuchsin, iodonitrotetrazolium (INT), tetrazolium blue and tetrazolium violet.

Alternatively, an enzyme can be used in a metallographic detection scheme. For example, SISH procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

In some embodiments, the signal-generating moiety is a fluorescent protein. Fluorescent proteins also can be used as a carrier, or can be coupled to a carrier, to facilitate visualization. For example, green fluorescent protein (GFP) was originally isolated from the light-emitting organ of the jellyfish *Aequorea victoria*. Chimeric GFP fusions can be expressed in situ by gene transfer into cells, and can be localized to particular sites within the cell by appropriate targeting signals. Spectral variants with blue, cyan and yellowish-green emissions have been successfully generated from the Aequorea GFP, but none exhibit emission maxima longer than 529 nm. GFP-like proteins have been isolated from Anthozoa (coral animals) that significantly expanded the range of colors available for biological applications. The family of 'GFP-like proteins' deposited in sequence databases now includes approximately 30 significantly different members. Fluorescent proteins refers to proteins that can become spontaneously fluorescent through the autocatalytic synthesis of a chromophore. Proteins that fluoresce at red or far-red wavelengths (red fluorescent proteins or RFPs) are known. RFPs can be used in combination with other fluorescent proteins that fluoresce at shorter wavelengths for both multicolor labeling and fluorescence resonance energy transfer (FRET) experiments. Commercially available RFPs are derived from two wild-type GFP-like proteins. DsRed (drFP583) has excitation and emission maxima at 558 nm and 583 nm, respectively. A far-red fluorescent protein was generated by mutagenesis of a chromoprotein that absorbs at 571 nm. HcRed1 (Clontech) has excitation and emission maxima at 588 nm and 618 nm, respectively. The fluorescent protein that emits fluorescence at the longest wavelength (without any mutations being introduced) is eqFP611, cloned from the sea anemone *Entacmaea quadricolor*. This protein absorbs at 559 nm and emits at 611 nm.

B. Use of Probes and Probe Systems

The present disclosure provides methods of using the disclosed probes and probe systems. For example, the probes can be used to detect and analyze a target nucleic acid molecule. In one example, the method includes contacting one or more of the disclosed target nucleic acid probes with a sample that includes nucleic acid molecules under conditions sufficient to permit hybridization between the nucleic acid molecules in the sample and the target nucleic acid probes. The sample is then contacted with the detection probe under conditions sufficient to permit hybridization between the detection probe and the target nucleic acid probes. The detection probe is then detected as described above.

The probes and probe systems of the present disclosure can be used for nucleic acid detection, such as in situ hybridization procedures (e.g., fluorescence in situ hybridization (FISH), chromogenic in situ hybridization (CISH) and silver in situ hybridization (SISH)). Hybridization between complementary nucleic acid molecules is mediated via hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. If a nucleotide unit at a certain position of a probe of the present disclosure is capable of hydrogen bonding with a nucleotide unit at the same position of a DNA or RNA molecule (e.g., a target nucleic acid sequence) then the oligonucleotides are complementary to each other at that position. The probe and the DNA or RNA are complementary to each other when a sufficient number of corresponding positions in each molecule are occupied by nucleotide units which can hydrogen bond with each other, and thus produce detectable binding. A probe need not be 100% complementary to its target nucleic acid sequence (e.g., genomic target nucleic acid sequence) to be specifically hybridizable. However sufficient complementarity is needed so that the probe binds, duplexes, or hybridizes only or substantially only to a target nucleic acid sequence when that sequence is present in a complex mixture (e.g., total cellular DNA or RNA).

In situ hybridization involves contacting a sample containing a target nucleic acid sequence (e.g., genomic target nucleic acid sequence) in the context of a metaphase or interphase chromosome preparation (such as a cell or tissue sample mounted on a slide) with a probe (i.e., the target nucleic acid probe described above) specifically hybridizable or specific for the target nucleic acid sequence (e.g., genomic target nucleic acid sequence). The slides are optionally pretreated, e.g., to remove paraffin or other materials that can interfere with uniform hybridization. The chromosome sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess target nucleic acid probe, and detection of specific labeling of the chromosome target is performed. According to some embodiments of the present disclosure, the detection is facilitated by hybridization of a detection probe to the target nucleic acid probe. The detection probe may be detected by direct detection or by indirect detection.

For example, in some direct detection embodiments, the detection probe is labelled with one or more fluorescent compounds, and the sample is analyzed by fluorescence microscopy or imaging. In some indirect detection embodiments, the detection probe comprises one or more detectable moieties comprising first members of a binding system (i.e., a hapten or biotin) which are detected by contacting the sample with second or second and third members of the binding system as described above. For a general description of in situ hybridization procedures, see, e.g., U.S. Pat. No. 4,888,278. Numerous procedures for fluorescence in situ hybridization (FISH), chromogenic in situ hybridization (CISH) and silver in situ hybridization (SISH) are known in the art. For example, procedures for performing FISH are described in U.S. Pat. Nos. 5,447,841, 5,472,842, 5,427,932, and for example, in Pinkel et al., Proc. Natl. Acad. Sci. 83:2934-2938, 1986; Pinkel et al., Proc. Natl. Acad. Sci. 85:9138-9142, 1988, and Lichter et al., Proc. Natl. Acad. Sci. 85:9664-9668, 1988. CISH is described in, e.g., Tanner et al., Am. J. Pathol. 157:1467-1472, 2000, and U.S. Pat. No. 6,942,970. Additional detection methods are provided in U.S. Pat. No. 6,280,929. Exemplary procedures for detecting viruses by in situ hybridization can be found in Poddighe et al., *J. Clin. Pathol.* 49:M340-M344, 1996.

Numerous reagents and detection schemes can be employed in conjunction with FISH, CISH, and SISH procedures to improve sensitivity, resolution, or other desirable properties. In some embodiments, the detection probe, or specific binding agent (such as an antibody, e.g., a primary antibody, receptor or other binding agent) comprises an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and 2010/0136652.

In other embodiments, detection probes labeled with fluorophores (including fluorescent dyes and semi-conductor nanocrystals) can be directly optically detected when performing FISH. Alternatively, the detection probe can be labeled with a non-fluorescent molecule, such as a hapten (such as the following non-limiting examples: biotin, digoxygenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Detection probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., semi-conductor nanocrystal) or with another indirectly detectable moiety, or can be contacted with one or more additional specific binding agents (e.g., secondary or specific antibodies), which can in turn be labeled with a fluorophore. Optionally, the detectable label is attached directly to the antibody, receptor (or other specific binding agent). Alternatively, the detectable label is attached to the binding agent via a linker, such as a hydrazide thiol linker, a polyethylene glycol linker, or any other flexible attachment moiety with comparable reactivities. For example, a specific binding agent, such as an antibody, a receptor (or other anti-ligand), avidin, or the like can be covalently modified with a fluorophore (or other label) via a heterobifunctional polyalkylene glycol linker such as a heterobifunctional polyethylene glycol (PEG) linker. A heterobifunctional linker combines two different reactive groups selected, e.g., from a carbonyl-reactive group, an amine-reactive group, a thiol-reactive group and a photoreactive group, the first of which attaches to the label and the second of which attaches to the specific binding agent.

It will be appreciated by those of skill in the art that by appropriately selecting labeled detection probes and/or labeled binding pairs, multiplex detection schemes can be produced to facilitate detection of multiple target nucleic acid sequences or multiple portions of a target nucleic acid sequence (e.g., genomic target nucleic acid sequences) in a single assay (e.g., on a single cell or tissue sample or on more than one cell or tissue sample). For example, in preferred embodiments, a first detection probe that corresponds to a first portion of the target sequence can be labeled with a first hapten, such as DIG, a second detection probe that corresponds to a second portion of the target nucleic acid sequence can be labeled with a second hapten, such as DNP, and a third detection probe that corresponds to a third portion of the target nucleic acid sequence can be labeled with a third hapten, such as NP. Following exposure of the sample to the probe sets, the bound probes can be detected by second or second and third members of the binding system. Standard light or fluorescent microscopes are an inexpensive tool for the detection of reagents and probes incorporating colorimetric or fluorescent compounds.

One preferred embodiment is an example of the approach shown in FIG. 3, which shows a detection scheme for detecting an ALK translocation. The three probes in FIG. 3 are each labeled with a different detectable moiety, in this example different haptens. The first nucleic acid probe to the 5' non-coding region of the target is labeled with DIG. The second nucleic acid probe to the 3' non-coding region of the target is labeled with DNP. The third nucleic acid probe which spans the presumptive breakpoint is labeled with NP. After hybridization, the three distinct probes can be detected with different signal generating systems, for example, with colorimetric reagents, fluorescent agents, semi-conductor nanocrystals, or other suitable signal generating moieties. FIG. 6(A-B) shows the use of colorimetric reagents to generate signals specific for each of the three probes. In the exemplary system, the reagents are applied sequentially. However, with other systems, the reagents can be added simultaneously if appropriate. In one example, the sample is contacted with a mouse anti-NP antibody. The sample is then contacted with a goat anti-mouse antibody that is conjugated to horse radish peroxidase. The sample is then contacted with reagents for silver detection. This generates a signal for the third nucleic acid probe. The sample is then contacted with a mouse anti-DIG antibody. Next, the sample is contacted with a goat anti-mouse antibody conjugated to alkaline phosphatase. The sample is then contacted with reagents for fast blue detection. This generates a signal for the first nucleic acid probe. The sample is then contacted with reagents to block alkaline phosphatase activity. Next the sample is contacted with a rabbit anti-DNP antibody followed by a goat ant-rabbit antibody conjugated to alkaline phosphatase. The sample is then contacted with reagents for fast red detection. This generates a signal for the second nucleic acid probe. Following these detection steps, the sample can be analyzed by microscopy for simultaneous visualization of signals specific for each of the three probes as described above. The resulting image that can be generated using this approach is shown in FIG. 6(A-B).

It will be appreciated by those of skill in the art that the detection systems and reagents described above, as well as other reagents and detection systems known in the art, may be substituted for these exemplary reagents. For example, alternative systems could use direct labeled nucleic acid probes, labeled first antibodies, or different combinations of first and second antibodies. Signal generating moieties used to label the probes or antibodies could be selected from, for example, other colorimetric reagents, fluorescent molecules, luminescent molecules, and semi-conductor nanocrystals. It will be appreciated that there are a number of different schemes for generating detectable signals specific for each of the three probes utilized in the described probe systems.

C. Targets

A target nucleic acid sequence according to the present disclosure can any sequence that comprises a chromosomal breakpoint involved in a chromosomal translocation event. In particular embodiments, the target sequence is a genomic target sequence or genomic subsequence, for example from a eukaryotic genome, such as a human genome. Target nucleic acid probes can be generated which correspond to essentially any genomic target sequence that includes at least a portion of unique non-repetitive DNA.

In some embodiments, the target nucleic acid molecule can be a sequence associated with (e.g., correlated with, causally implicated in, etc.) a disease. In some embodiments, a target sequence is selected that is associated with a disease or condition, such that detection of hybridization can be used to infer information (such as diagnostic or prognostic information for the subject from whom the sample is obtained) relating to the disease or condition. In certain embodiments, the selected target nucleic acid molecule is a target nucleic acid molecule associated with a neoplastic disease (or cancer). In some embodiments, the genomic target sequence is a sequence that comprises a chromosomal breakpoint associated with a chromosomal translocation associated with a cancer. Examples of such translocations include those identified in the Atlas of Genetics and Cytogenetics in Oncology and Haematology, available on the world wide web at atlasgeneticsoncology.org//Anomalies/Anomliste.

The target nucleic acid sequence (e.g., genomic target nucleic acid sequence) can span any number of base pairs. In some embodiments, the target nucleic acid sequence spans at least 1000 base pairs. In specific examples, a target nucleic acid sequence (e.g., genomic target nucleic acid sequence) is at least 10,000, at least 50,000, at least 100,000, at least 150,000, at least 250,000, or at least 500,000 base pairs in length (such as 100 kb to 600 kb, 200 kb to 500 kb, or 300 kb to 500 kb). In examples, where the target nucleic acid sequence is from a eukaryotic genome (such as a mammalian genome, e.g., a human genome), the target sequence typically represents a small portion of the genome (or a small portion of a single chromosome) of the organism (for example, less than 20%, less than 10%, less than 5%, less than 2%, or less than 1% of the genomic DNA (or a single chromosome) of the organism).

In some embodiments, the information derived from analysis of the hybridization of the probes to the target sequence is used to make a diagnosis or prognosis related to an outcome for cancer. In some embodiments, the cancer is non-small cell lung cancer and the rearrangement is an ALK rearrangement. Oncogenic rearrangements of the anaplastic lymphoma kinase (ALK) gene occur in some non small-cell lung cancers (NSCLC). The chromosomal rearrangements that interrupt the ALK gene and fuse it with another gene result in the creation of oncogenic ALK fusion genes. In turn, these enhance cell proliferation and survival. In some embodiments, the ALK fusion gene is ALK-EML4.

In some embodiments, where the assays indicate an ALK rearrangement, the information is used to select a therapeutic treatment for the patient depending on the presence and type of the ALK rearrangement. In some embodiments, the therapeutic treatment is administration of an ALK inhibitor. Examples of ALK inhibitors include, but are not limited to, PF02341066 (Pfizer).

D. Kits

In some embodiments, the present disclosure provides kits including at least the first, second and third nucleic acid probes. In some embodiments, the first nucleic acid probe hybridizes to a portion of the chromosome that is 5' to a chromosomal breakpoint, the second nucleic acid probe hybridizes to a portion of the chromosome that is 3' to the chromosomal breakpoint, and the third nucleic acid probe comprises a 5' portion and a 3' portion and which hybridizes to 5' and 3' sequences adjacent to the chromosomal breakpoint so that the third nucleic acid probes spans the chromosomal breakpoint in the absence of a translocation. In some embodiments, kits for in situ hybridization procedures such as FISH, CISH, and/or SISH include at least first second and third target nucleic acid probes as described herein. In some embodiments, the kits further include one or more detection reagents for use in conjunction with the at least one target nucleic acid probes. In some embodiments, the kits further include at least one specific binding agent for use in conjunction with the first, second and third nucleic acid probes. Accordingly, kits can include one or more target nucleic acid probes, one or more detection probes, and one or more specific binding agents.

The kits can also include one or more reagents for performing an in situ hybridization assay, or for producing a probe. For example, a kit can include at least one nucleic acid molecule (or population of such molecules), along with one or more buffers, labeled dNTPs, a labeling enzyme (such as a polymerase), primers, nuclease free water, and instructions for producing a labeled probe.

In one example, the kit includes first, second and third nucleic acid probes and one or more specific binding agents along with buffers and other reagents for performing in situ hybridization such as paraffin pretreatment buffer, protease(s) and protease buffer, prehybridization buffer, hybridization buffer, wash buffer, counterstain(s), mounting medium, or combinations thereof. The kit can optionally further include control slides for assessing hybridization and signal of the probe.

E. Automation

A person of ordinary skill in the art will appreciate that embodiments of the method disclosed herein for using hapten conjugates can be automated. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. published application Nos. 20030211630 and 20040052685, each of which is incorporated herein by reference. Particular embodiments of polymeric hapten staining procedures can be conducted using various automated processes.

Additional details concerning exemplary working embodiments are provided in the working examples.

EXAMPLES

Example 1

Materials and Methods

ALK Triple Probe Design

The break-apart in situ hybridization (ba-ISH) assay is designed to assess the arrangements of the ALK gene loci (ALK-EML4 fusion). Three probes are generated to hybridize with the neighboring centromeric region (770 kb) and telomeric region (683 kb) of the ALK gene and ALK gene region (728 Kb) (FIG. 1). ALK gene probe is labeled with NP hapten, 5'ALK probe is labeled with DIG hapten, and 3' ALK probe is labeled with DNP hapten.

Automated Brightfield Break-Apart In Situ Hybridization Protocol

All optimization and performance evaluation for brightfield in situ hybridization ALK gene ba-ISH assay are conducted with the BenchMark® XT automated slide processing system (Ventana Medical Systems, Inc., Tucson, Ariz.). The ba-ISH instrument software is created so that all steps from baking to counterstaining can be conducted without interruption. The slides are baked on the instrument at 65° C. for 20 minutes to melt paraffin followed by Liquid Coverslip (Ventana Medical Systems, Inc.) primed EZ Prep (Ventana Medical Systems, Inc.) deparaffinization step. DNA targets are retrieved by the combination of heat-treatment with Cell Conditioning 2 (acidic pH citrate buffer, Ventana Medical Systems, Inc.) and tissue digestion with ISH Protease 2 or ISH Protease 3 (Ventana Medical Systems, Inc.). Appropriate protease digestion time is determined for each tissue sample due to different tissue fixation and processing conditions of clinical samples. The cocktail of 5' and 3' ALK and ALK probes is formulated with human placental DNA (2 mg/ml) in a Ventana hybridization buffer. The probes and target DNA are co-denatured at 85° C. for 20 minutes and hybridization is conducted at 44° C. for 5 hours. Stringency wash steps are conducted at 72° C. with 2×SSC (Ventana Medical Systems, Inc.). The sequence of ISH signal detection is performed with: 1) horseradish peroxidase (HRP)-based silver detection; 2) alkaline phosphatase (AP)-based blue detection; and 3) AP-based red detection. NP hapten is detected with mouse anti-NP antibody followed by HRP-conjugated goat anti-mouse antibody. HRP enzyme is colored with silver acetate, hydroquinone, and $H_2O_2$ (ultraView SISH Detection Kit, Ventana Medical Systems, Inc.). DIG hapten is labeled with mouse anti-DIG antibody, the anti-DIG antibody is reacted with AP-conjugated goat anti-mouse antibody, and AP enzyme is colored with fast blue detection. Then, the AP enzyme is denatured with the hybridization buffer for 30 minutes at 37° C. After washing the slides with 2×SSC, the third ISH detection is performed. DNP hapten is labeled with rabbit anti-DNP antibody, the DNP antibody is reacted with AP-conjugated goat anti-rabbit antibody, and AP enzyme is colored with a fast red detection (ultraView Red ISH Detection Kit, Ventana Medical Systems, Inc.). All slides are counterstained with Hematoxylin II (Ventana Medical Systems, Inc.) and Bluing Reagent (Ventana Medical Systems, Inc.). Counterstained slides are rinsed with distilled water containing DAWN® (Proctor & Gamble Company, Cincinnati, Ohio) for cleaning the slides. Finally, air-dried slides are coverslipped with Tissue-Tek® film coverslipper (Sakura Finetek Japan, Tokyo, Japan).

Example 2

The following example describes the a process for analysis of an ALK rearrangement with a three color break apart probe system. The slides were baked on the instrument at 65° C. for 20 minutes to melt paraffin followed by Liquid Coverslip (Ventana Medical Systems, Inc.) primed EZ Prep (Ventana Medical Systems, Inc.) deparaffinization step. DNA targets were retrieved by the combination of heat-treatment with a citrate buffer based target retrieval solution CC2 (Ventana Medical Systems, Inc.) and tissue digestion with ISH Protease 2 (Ventana Medical Systems, Inc.). Appropriate protease digestion time was determined for each tissue sample due to different tissue fixation and processing conditions of clinical samples. The cocktail of 3 ALK probes (DNP-labeled 5'ALK probe, fluorescein-labeled internal ALK probe, and DIG-labeled 3'ALK probe, 12 µg/ml each) was formulated with fish DNA in a Ventana hybridization buffer. The probes and target DNA were co-denatured at 85° C. for 20 minutes and hybridization was conducted at 44° C. for 5 hours. Stringency wash steps were conducted at 72° C. with 2×SSC (Ventana Medical Systems, Inc.). Fluorescein-labeled internal ALK probe was visualized with DAB detection after incubating with mouse anti-fluorescein antibody followed by HRP-conjugated goat anti-mouse antibody. DNP hapten on 5'ALK probe was labeled with rabbit anti-DNP antibody, the anti-DNP antibody was reacted with AP-conjugated goat anti-rabbit antibody, and AP enzyme was colored with a fast blue detection. Then, the AP enzyme was denatured with the hybridization buffer for 30 minutes at 37° C. After washing the slides with 2×SSC, the third ISH detection was performed. DIG hapten on 3'ALK probe was labeled with mouse anti-DIG antibody, the DIG antibody was reacted with AP-conjugated goat anti-mouse antibody, and AP enzyme was colored with a fast red detection. All slides were counterstained with diluted Hematoxylin II (Ventana Medical Systems, Inc.), 1:3 in water and Bluing Reagent (Ventana Medical Systems, Inc.). Counterstained slides were rinsed with distilled water containing DAWN® (Proctor & Gamble Company, Cincinnati, Ohio) for cleaning the slides. Finally, air-dried slides were coverslipped with Tissue-Tek® film coverslipper (Sakura Finetek Japan, Tokyo, Japan). The ba-ISH slides were analyzed and photographed with a Nikon ECLPSE 90i microscope (Nikon Instruments Inc., Melville, N.Y.) equipped with a Nikon digital camera DS-Fil (Nikon Instruments Inc.). The results are provided in FIG. 6(A-B).

According to the foregoing examples, the present disclosure provides methods for analyzing a sample suspected of having a chromosomal translocation associated with a breakpoint comprising contacting a first nucleic acid probe that hybridizes to a portion of the genomic DNA that is located 5' to the breakpoint, a second nucleic acid probe that hybridizes to a portion of the genomic DNA that is located 3' to the breakpoint, and a third nucleic acid probe that hybridizes to a portion of DNA that is adjacent to the breakpoint; establishing suitable conditions for the probes to hybridize to genomic DNA in the sample; and detecting hybridization of the probes to the genomic DNA in the sample. In some embodiments, the third nucleic acid probe further comprises a 5' portion and 3' portion, wherein the 5' portion hybridizes to a portion of the genomic DNA that is 5' and adjacent to the breakpoint and the 3' portion hybridizes to a portion of the genomic DNA that is 3' and adjacent to the breakpoint so that the third nucleic acid probe hybridizes to a region of the genomic DNA spanning the breakpoint in the absence of a rearrangement. In some embodiments, the third nucleic acid probe hybridizes to a portion of genomic DNA that is 5' and adjacent to the breakpoint so that in the presence of a rearrangement a signal detected for the first nucleic acid probe and a signal detected for the third nucleic acid probe have an orientation which is inverted as compared to the orientation of the signal detected for the first nucleic acid probe and the signal detected for the third nucleic acid probe in the absence of a rearrangement. In some embodiments, the third nucleic acid probe hybridizes to a portion of genomic DNA that is 3' and adjacent to the breakpoint so that in the presence of a rearrangement a signal detected for the second nucleic acid probe and a signal detected for the third nucleic acid probe have an orientation which is inverted as compared to the orientation of the signal detected for the second nucleic acid probe and the signal detected for the third nucleic acid probe in the absence of a rearrangement. In some embodiments, the nucleic acid probes comprise nucleic acid selected from the group consisting of RNA, DNA, PNA, LNA and combinations thereof.

What is claimed is:

1. A chromogenic in situ hybridization method for determining whether a sample comprises a chromosomal rearrangement, the chromosomal rearrangement occurring as a result of a breakpoint within a gene, comprising:
   contacting the sample with
   a first nucleic acid probe comprising a first sequence configured to hybridize to a first chromosomal DNA target located 5' to the breakpoint,
   a second nucleic acid probe comprising a second sequence configured to hybridize to a second chromosomal DNA target located 3' to the breakpoint, and
   a third nucleic acid probe comprising a third sequence having a 5' portion and a 3' portion, the 5' portion configured to hybridize to a portion of a third chromosomal DNA target that is 5' and adjacent to the breakpoint, and the 3' portion configured to hybridize to a portion of the third chromosomal DNA target that is 3' and adjacent to the breakpoint, such that in an absence of a rearrangement the third nucleic acid probe hybridizes to a region of the third chromosomal DNA target spanning the breakpoint;
   establishing conditions suitable for the first, second, and third probes to hybridize to the respective chromosomal DNA targets in the sample;
   contacting the sample with first, second, and third detection reagents, the first detection reagent comprising components to label the first chromosomal DNA target with a first chromogen, the second detection reagent comprising components to label the second chromosomal DNA target with a second chromogen, and the third detection reagent comprising components to label the third chromosomal DNA target with a third chromogen, where each of the first, second, and third chromogens provide different detectable signals;
   detecting a colocalization of a third signal from the third labeled chromosomal DNA target with a first signal from the first labeled chromosomal DNA target;
   detecting a colocalization of the third signal from the third labeled chromosomal DNA target with a second signal from the second labeled chromosomal DNA target; and
   identifying the chromosomal rearrangement based on the detected colocalizations.

2. The method of claim 1, further comprising identifying a sample order and orientation, the sample order and orientation being an arrangement of the first signal, the second signal, and the third signal.

3. The method of claim 1, wherein the gene is an ALK gene.

4. The method of claim 2, further comprising comparing the sample order and orientation with a control order and orientation.

5. The method of claim 4, wherein the comparing of the sample order and orientation with a control order and orientation includes establishing whether the sample order and orientation includes inversion of the first signal and the third signal as compared to the control order and orientation.

6. The method of claim 4, wherein the comparing of the sample order and orientation with a control order and orientation includes establishing whether the sample order and orientation includes inversion of the second signal and the third signal as compared to the control order and orientation.

7. The method of claim 4, the control order and orientation is determined by analyzing a control sample known to be devoid of the chromosomal rearrangement associated with cancer comprising,
   contacting the control sample with
   the first nucleic acid probe comprising the first sequence configured to hybridize to genomic DNA located 5' to the breakpoint,
   the second nucleic acid probe comprising the second sequence configured to hybridize to genomic DNA located 3' to the breakpoint, and
   the third nucleic acid probe comprising the third sequence configured to hybridize to genomic DNA adjacent to and spanning the breakpoint;
   establishing conditions suitable for the probes to hybridize to the genomic DNA in the control; and
   detecting hybridization of the probes by detecting a first signal associated with the first nucleic acid probe, a second signal associated with the second nucleic acid probe, and a third signal associated with the third nucleic acid probe.

8. The method of claim 1, wherein nucleic acid probes comprise nucleic acids selected from the group consisting of RNA, DNA, PNA, LNA and combinations thereof.

9. The method of claim 8, wherein the first nucleic acid probe is conjugated to a first, hapten, the second nucleic acid probe is conjugated to a second hapten, and the third nucleic acid probe is conjugated to a third hapten, wherein each of the first, second, and third haptens are different.

10. The method of claim 9, wherein the different first, second and third haptens are selected from the group consisting of biotin, 2,4-dintropheyl (DNP), fluorescein derivatives, digoxygenin (DIG), 5-nitro-3-pyrozolecarbamide (nitropyrazole, NP), 4,5,-dimethoxy-2-nitrocinnamide (nitrocinnamide, NCA), 2-(3,4-dimethoxyphenyl)-quinoline-4-carbamide (phenylquinolone, DPQ), 2,1,3-benzoxadiazole-5-carbamide (benzofurazan, BF), 3-hydroxy-2-quinoxalinecarbamide (hydroxyquinoxaline, HQ), 4-(dimethylamino) azobenzene-4'-sulfonamide (DABSYL), rotenone isoxazoline (Rot), (E)-2-(2-(2-oxo-2,3-dihydro-1H-benzo [b][1,4]diazepin-4-yl)phenozy)acetamide (benzodiazepine, BD), 7-(diethylamino)-2-oxo-2H-chromene-3-carboxylic acid (coumarin 343, CDO), 2-acetamido-4-methyl-5-thiazolesulfonamide (thiazolesulfonamide, TS), and p-methoxyphenylpyrazopodophyllamide (Podo).

11. The method of claim 9, wherein the first, second, and third detection reagents comprise antibodies specific for the first, second, and third haptens, respectively, where each antibody conjugated to an enzyme.

12. The method of claim 11, wherein the first, second, and third detection reagents further comprise first, second, and third chromogenic substrates, respectively.

13. A chromogenic in situ hybridization method for determining whether a sample comprises a chromosomal rearrangement associated with cancer, the chromosomal rearrangement occurring as a result of a breakpoint within a gene, comprising:
contacting the sample with
a first nucleic acid probe comprising a first sequence configured to hybridize to a first chromosomal DNA target located 5' to the breakpoint, the first nucleic acid probe conjugated to a first hapten;
a second nucleic acid probe comprising a second sequence configured to hybridize to a second chromosomal DNA target located 3' to the breakpoint, the second nucleic acid probe conjugated to a second hapten;
a third nucleic acid probe comprising a third sequence having a 5' portion and a 3' portion, the 5' portion configured to hybridize to a portion of a third genomic DNA target that is 5' and adjacent to the breakpoint, and the 3' portion configured to hybridize to a portion of the third chromosomal DNA target that is 3' and adjacent to the breakpoint, such that in an absence of a rearrangement the third nucleic acid probe hybridizes to a region of the third chromosomal DNA target spanning the breakpoint, the third nucleic acid probe conjugated to a third hapten;
establishing conditions suitable for the first, second, and third probes to hybridize to the respective chromosomal DNA targets in the sample;
contacting the sample with first, second, and third antibodies that are specific to the first, second, and third haptens, respectively, and wherein the first, second, and third antibodies are each conjugated to an enzyme;
contacting the sample with first, second, and third chromogenic substrates, to provide first, second, and third labeled chromosomal DNA targets, wherein each of the chromogenic substrates provide different signals;
detecting a colocalization of a third signal from the third labeled chromosomal DNA target with a first signal from the first labeled chromosomal DNA target;
detecting a colocalization of the third signal from the third labeled chromosomal DNA target with a second signal from the second labeled chromosomal DNA target; and
identifying the chromosomal rearrangement based on the detected colocalizations.

* * * * *